US 6,733,435 B2

(12) United States Patent
Cañedo

(10) Patent No.: US 6,733,435 B2
(45) Date of Patent: May 11, 2004

(54) ELECTROMAGNETIC METHOD OF TREATMENT OF LESIONS ASSOCIATED WITH INADEQUATE BLOOD PERFUSION, PARTIAL DENERVATION, TISSUE LOSS, PAIN, EDEMA, INFLAMMATION AND INFECTION

(76) Inventor: Luis Cañedo, Luz San Luan 209, Colonia del Yalle C.P. 03001 (MX)

( * ) Notice: Subject to any disclaimer, the term of this patent is extended or adjusted under 35 U.S.C. 154(b) by 0 days.

(21) Appl. No.: 10/092,801

(22) Filed: Mar. 8, 2002

(65) Prior Publication Data

US 2003/0171640 A1 Sep. 11, 2003

(51) Int. Cl.[7] ................................................. A61N 2/00
(52) U.S. Cl. ............................................................ 600/9
(58) Field of Search .................... 600/9–15; 128/897–98

(56) References Cited

U.S. PATENT DOCUMENTS

| | | |
|---|---|---|
| 3,890,953 A | 6/1975 | Kraus et al. |
| 4,683,873 A | 8/1987 | Cadossi et al. |
| 5,092,835 A | 3/1992 | Schurig et al. |
| 5,106,361 A | 4/1992 | Liboff et al. |
| 5,123,898 A | 6/1992 | Liboff et al. |
| 5,131,904 A | 7/1992 | Markoll |
| 5,160,591 A | 11/1992 | Liboff et al. |
| 5,183,456 A | 2/1993 | Liboff et al. |
| 5,267,939 A | 12/1993 | Liboff et al. |
| 5,314,401 A | 5/1994 | Tepper |
| 5,318,561 A | 6/1994 | McLeod et al. |
| 5,441,495 A | 8/1995 | Liboff et al. |
| 5,453,073 A | 9/1995 | Markoll |
| 5,496,258 A | 3/1996 | Anninos et al. |
| 5,752,911 A * | 5/1998 | Canedo et al. .................. 600/9 |
| 6,290,638 B1 * | 9/2001 | Canedo et al. .................. 600/9 |

FOREIGN PATENT DOCUMENTS

| | | |
|---|---|---|
| WO | WO 01/15770 A2 | 3/2001 |
| WO | WO 01/15770 A3 | 9/2001 |

* cited by examiner

Primary Examiner—John P. Lacyk
(74) Attorney, Agent, or Firm—Cahn & Samuels, LLP

(57) ABSTRACT

A method of treating a body lesion associated with inadequate blood perfusion, partial denervation, tissue loss, pain, edema, and/or infection, comprising applying to a subject afflicted with a lesion, externally and non-invasively at a site removed from the lesion, analgesic, angiogenic, vasculogenic, nerve growth, osteogenic, anti-edema, anti-inflammation and/or wound repair effective electromagnetic fields (EMFs) comprising frequencies of a few Hertz to less than about 300 Hz and static magnetic field components from a few microTesla to a maximum intensity of about 0.3 to about 0.8 mT. used alone or in combination with a homogeneous static magnetic field of about 40 to about 80 mT or about 400 to about 800 gauss.

66 Claims, 16 Drawing Sheets

ELECTROMAGNETIC METHOD OF TREATMENT OF LESIONS ASSOCIATED WITH INADEQUATE BLOOD PERFUSION, PARTIAL DENERVATION, TISSUE LOSS, PAIN, EDEMA, INFLAMMATION AND INFECTION

BACKGROUND OF THE INVENTION

1. Field of the Invention

The present invention relates generally to a method for treatment of skin lesions and internal wounds such as viable but underperfused myocardium. More specifically, this invention is related to a method for treatment of a subject afflicted with inadequate blood perfusion, tissue loss, partial denervation, wounds, bone fractures, burns and/or ulcers, by administration of time varying electromagnetic fields alone or simultaneously with static magnetic fields to the subject of specific characteristics.

2. Description of the Background

Locally applied electromagnetic fields (EMFs) have been shown to increase skin and nerve regeneration, collagen maturation and tensile strength during healing of skin wounds in a rat. In vitro, EMFs have been shown also to induce the proliferation and collagen-mediated production of fibroblasts and foster angiogenesis. In addition, locally applied EMFs have long been known to promote soft tissue repair. Chronic venous leg ulcers and pressure ulcers have been treated by application of various therapies, including the local application of growth factors, hyperbaric oxygen, local infrared irradiation, EMFs, ultra violet and low energy lasers as well as ultrasound, directly to the ulcerated site. The Agency for Health Care Policy and Research of the U.S. Department of Health and Human Services, however, recommended locally applied EMFs as the sole adjunctive therapy with sufficient supporting evidence for the treatment of pressure ulcers. Although the local application of EMFs has been used to treat chronic venous leg ulcers, nerve regeneration, bone nonunionis and to protect animal models from the sequela of provoked ischemia, all attempts to attain healing by administration of EMFs at a point distant from the afflicted site have failed up to the present time.

The ability of treating wounds and other ailments without administering the EMFs at the wound site while attaining an improvement, and even full healing of the wound, would be of great help, particularly in cases where the wound site is somewhat inaccessible or simply to avoid inconveniencing the patient. Such treatment could be administered on an out-patient basis, would not require highly skilled personnel and would reduce the cost of treatment while freeing medically trained personnel for the diagnosis and prescription of therapies and for following up the results attained in any particular round of applications.

Accordingly, there is a clear need for an improved method for accelerating and fostering of healing of a subject's wounds, particularly those wounds that prove to be resistant to other more conventional treatments, which is simple, does not inconvenience the subject, may be performed on an out-patient's basis by non-highly skilled personnel, and that does not inconvenience the patient. Such treatment would be highly therapeutic and cost effective.

SUMMARY OF THE INVENTION

This invention relates to a method of treating lesions, burns, skin ulcers, and viable but underperfused myocardium, which comprises applying externally and non-invasive extremely low frequency electromagnetic fields (EMFs) of specific characteristics to a subject afflicted with a lesion burn and ulcer, at a site removed from the site of the lesion under conditions effective to accelerate lesion, burn, bone or ulcer healing, to enhance angiogenesis and vasculogenesis and to improve the effect of other subsequently applied therapies. Suitable EMFs comprise a time-varying electromagnetic field component generated at frequencies of a few Hertz (more than one) to less than about 300 Hz and static magnetic field components having an intensity of about few micro Tesla, e.g., about 2–5 $\mu$T, about 20 $\mu$T to about 100 $\mu$T, about 0.3 mT, about 0.8 mT. These EMFs may be used alone or in combination with a homogeneous static magnetic field of about 40, about 50 to about 70, about 80 mT (or about 400, about 500 to about 700, about 800 Gauss). Although in some cases, the measured frequencies inside the coils are about 0.3 to about 0.8 $\mu$T, in those areas of the skin close but not inside the coils, the intensities of the EMF are progressively reduced down to the environmental magnetic fields.

The method of this invention is particularly suited for the therapeutic treatment of subjects afflicted with skin lesions such as burns, internal wounds such as bone fractures, partial denervation, and ulcers, particularly chronic wounds, such as venous and arterial leg ulcers, pressure ulcers, unhealing wounds, infected wounds, painful inflamed tissue, areas of inadequate blood perfusion, such as viable but underperfused myocardium and the like, which are present either by themselves or in association with other causes, e.g. atherosclerosis, varicose veins, diabetes, hypertension, rheumatoid arthritis, trauma, and the like. Some lesions are resistant or non-responsive to treatment with surgical or conservative conventional methods, but the administration of the present therapy makes them highly responsive to previously ineffective treatments. The present method may be administered for a short period of time as well as through periodically exposing an already treated subject to repeated treatments over a period of time effective for reducing the intensity of pain, edema, inflammation and infection, increasing angiogenesis, vasculogenesis, nerve regeneration, bone union and reestablishing the subject's own immune-mediated anti-inflammatory response and wound healing processes.

The present therapeutic method greatly reduces the healing time in subjects who had proved previously highly resistant to other conventional medical treatments.

The present invention will be further illustrated by reference to the various drawings and the several examples hereinafter described.

BRIEF DESCRIPTION OF THE DRAWINGS

There are two preferred ways to expose a body part to the magnetic fields of the present invention. The first way utilizes a design to combine time-varying magnetic fields with static magnetic fields. Two different embodiments of the apparatus of this invention related to the first design are provided for this purpose.

The first embodiment of this design of the apparatus is described in FIGS. 1 to 7.

Figure 1:
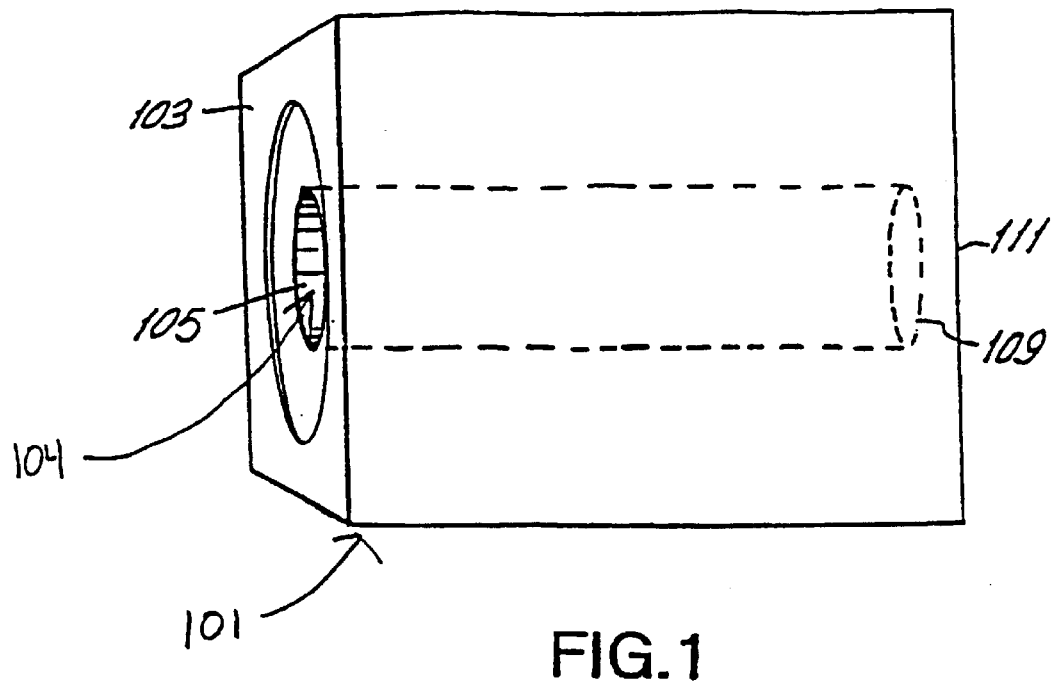
FIG. 1 depicts a simplified partial perspective view of the apparatus of the present invention as viewed from the outside.
Figure 2:
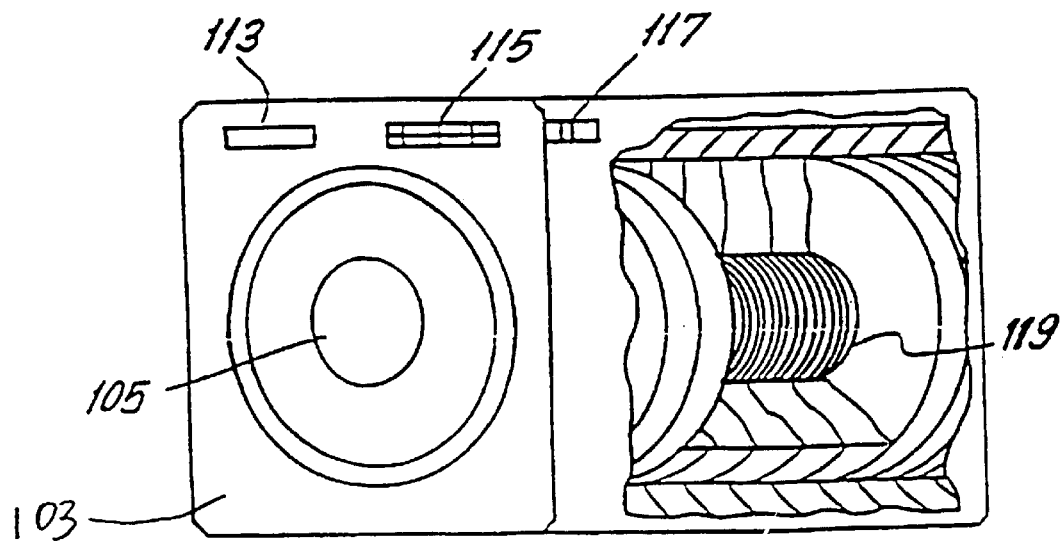
FIG. 2 depicts a partial perspective and sectional view of the apparatus shown in FIG. 1.
Figure 8:
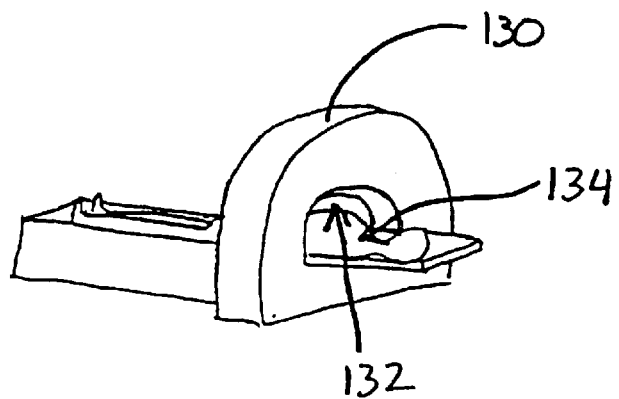
Figure 9:
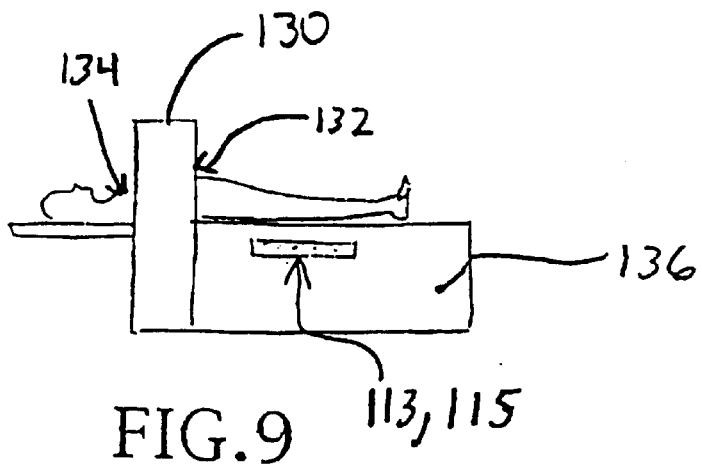
Figure 10:
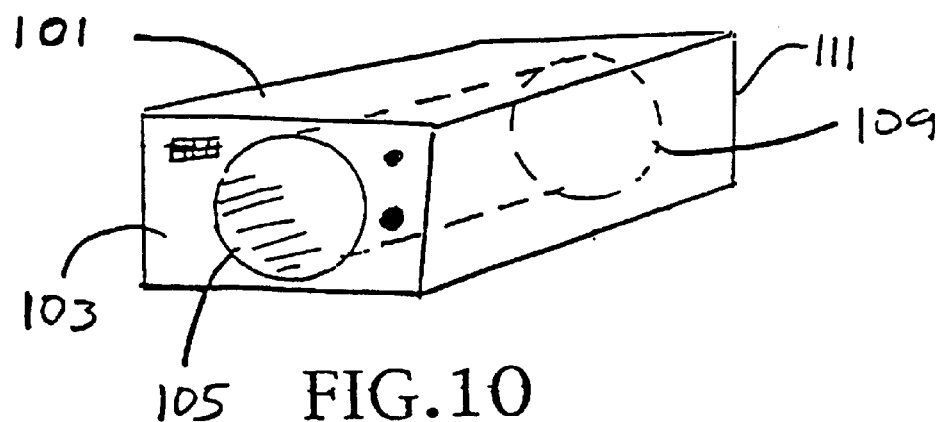

The second embodiment of the first design of the apparatus of the invention is shown in FIGS. 8 to 10, This embodiment is al enlarged version of the first embodiment shown in FIGS. 1 and 2.

FIG. 8 depicts a perspective view of the apparatus of the present invention exposing a human body to EMFs.

FIG. 9 depicts a side perspective view of the apparatus shown in FIG. 8.

A second design of the apparatus of the invention exposes the body part only to the time-varying magnetic fields. Five different embodiments of the apparatus of this invention are exemplified for this purpose.

The first of the five embodiments is shown in FIGS. 10 to 13. In this embodiment, the permanent magnets of the apparatus described above are eliminated while the other components remain unchanged.

FIG. 10 depicts a simplified partly perspective view of the apparatus of the present invention as viewed from the outside.

Figure 11:
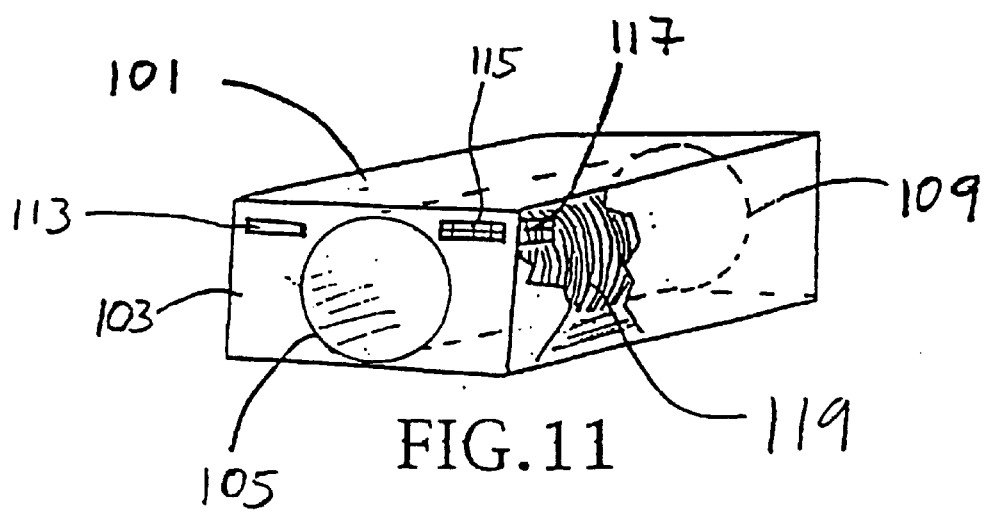

FIG. 11 depicts a partial perspective and sectional view of the apparatus shown in FIG. 10.

Figure 12:
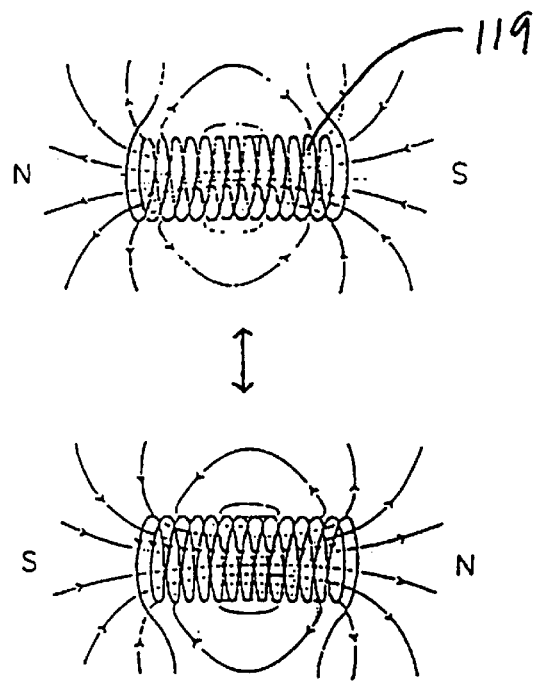

FIG. 12 shows a schematic representation of the electromagnetic flux generated by the time-varying magnetic fields in accordance with this invention.

Figure 13:
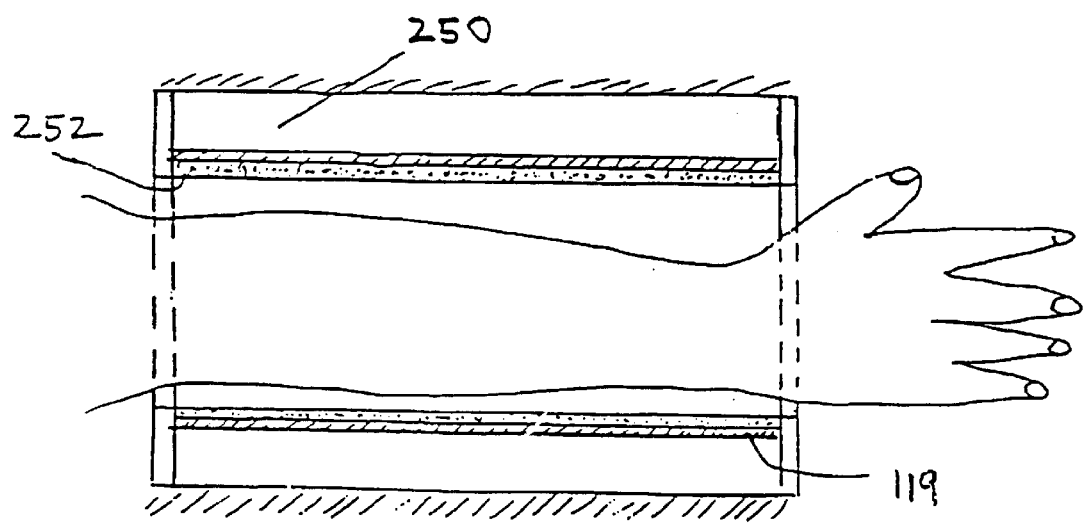

FIG. 13 is a simplified schematic top view of an arm extended between the magnetic coils such as the coils shown in FIG. 11.

Figure 14:
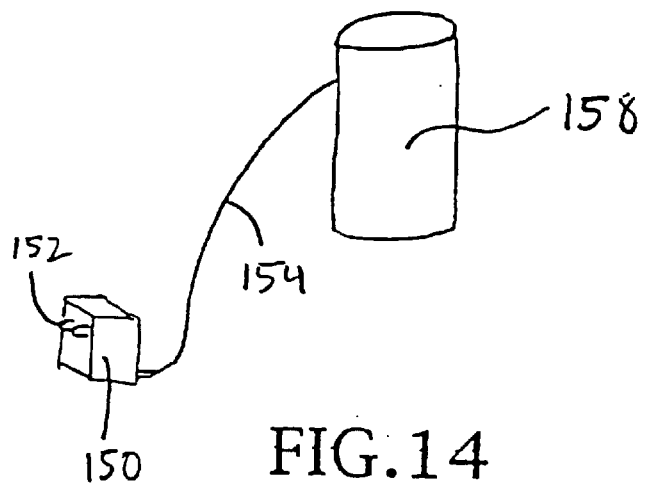
Figure 15:
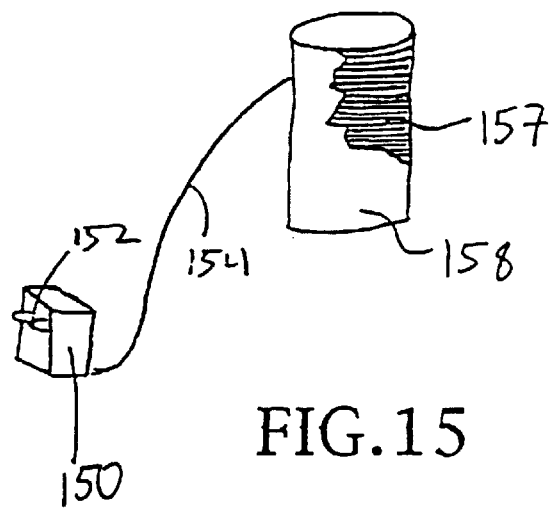
Figure 16:
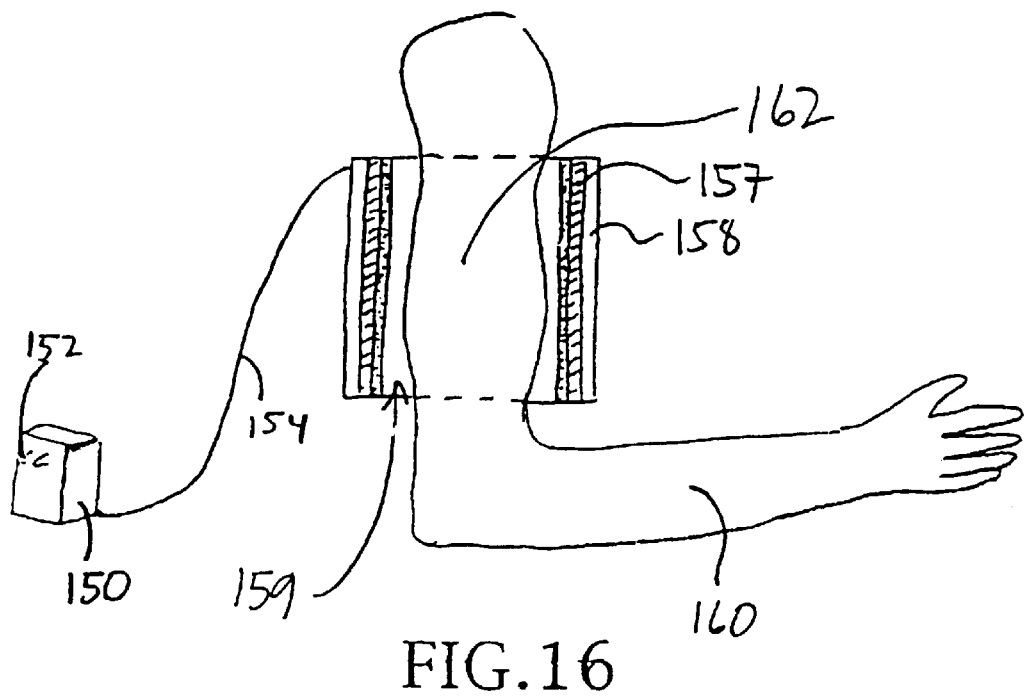

The second of the five embodiments is shown in FIGS. 14 to 16. This is a simplified version of the embodiment shown in FIGS. 10 to 13.

FIG. 14 depicts a simplified perspective view of the apparatus of the present invention as viewed from the outside.

FIG. 15 depicts a partial perspective and sectional view of the apparatus shown in FIG. 14.

FIG. 16 is a simplified schematic top view of an arm extended between the magnetic coils such as the coils shown in FIG. 15.

Figure 17:
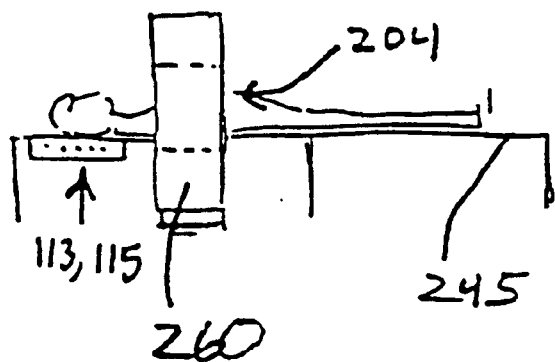
Figure 18:
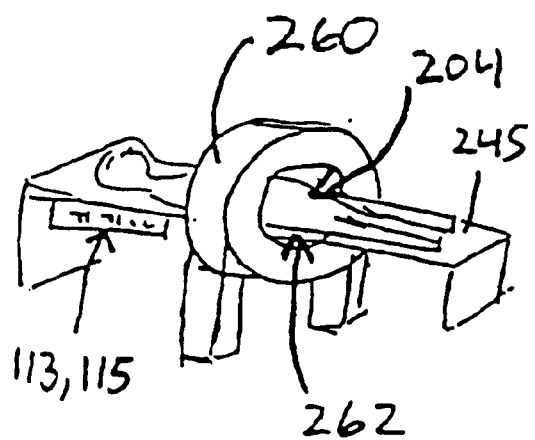

The third of the five embodiments is shown in FIGS. 17 and 18, and is an enlarged version of the embodiment shown in FIGS. 10 to 13.

FIG. 17 depicts a side perspective view of the apparatus of the present invention exposing a body to EMFs.

FIG. 18 depicts a perspective view of the apparatus shown in FIG. 17.

In the fourth of the five embodiments of the apparatus of this invention, the time-varying magnetic fields of the present invention are generated by two Hemholtz coils.

FIGS. 19 to 23 describe this embodiment.

Figure 19:
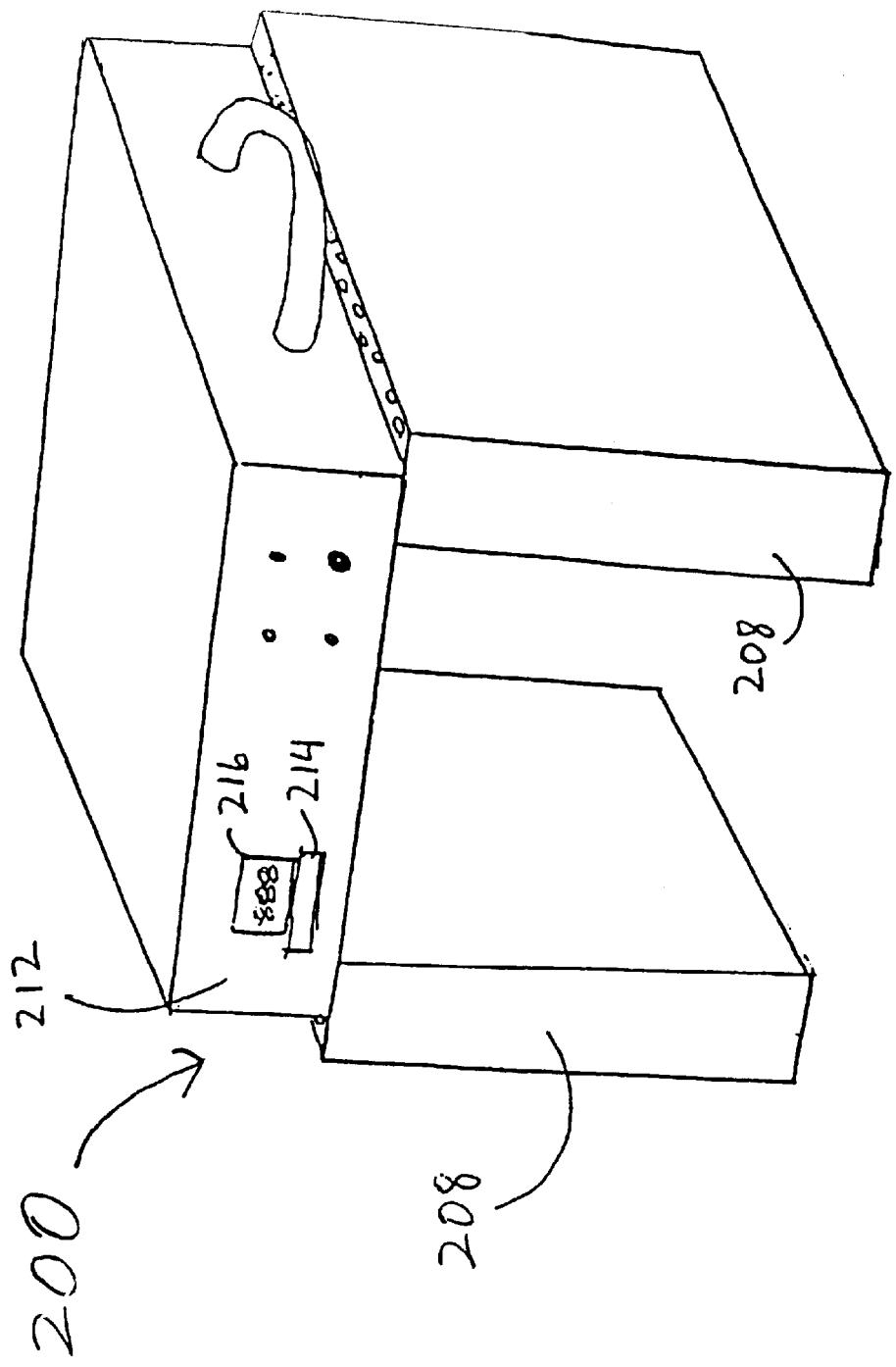

FIG. 19 depicts a simplified perspective view of the apparatus of the present invention as viewed from the outside.

Figure 20:
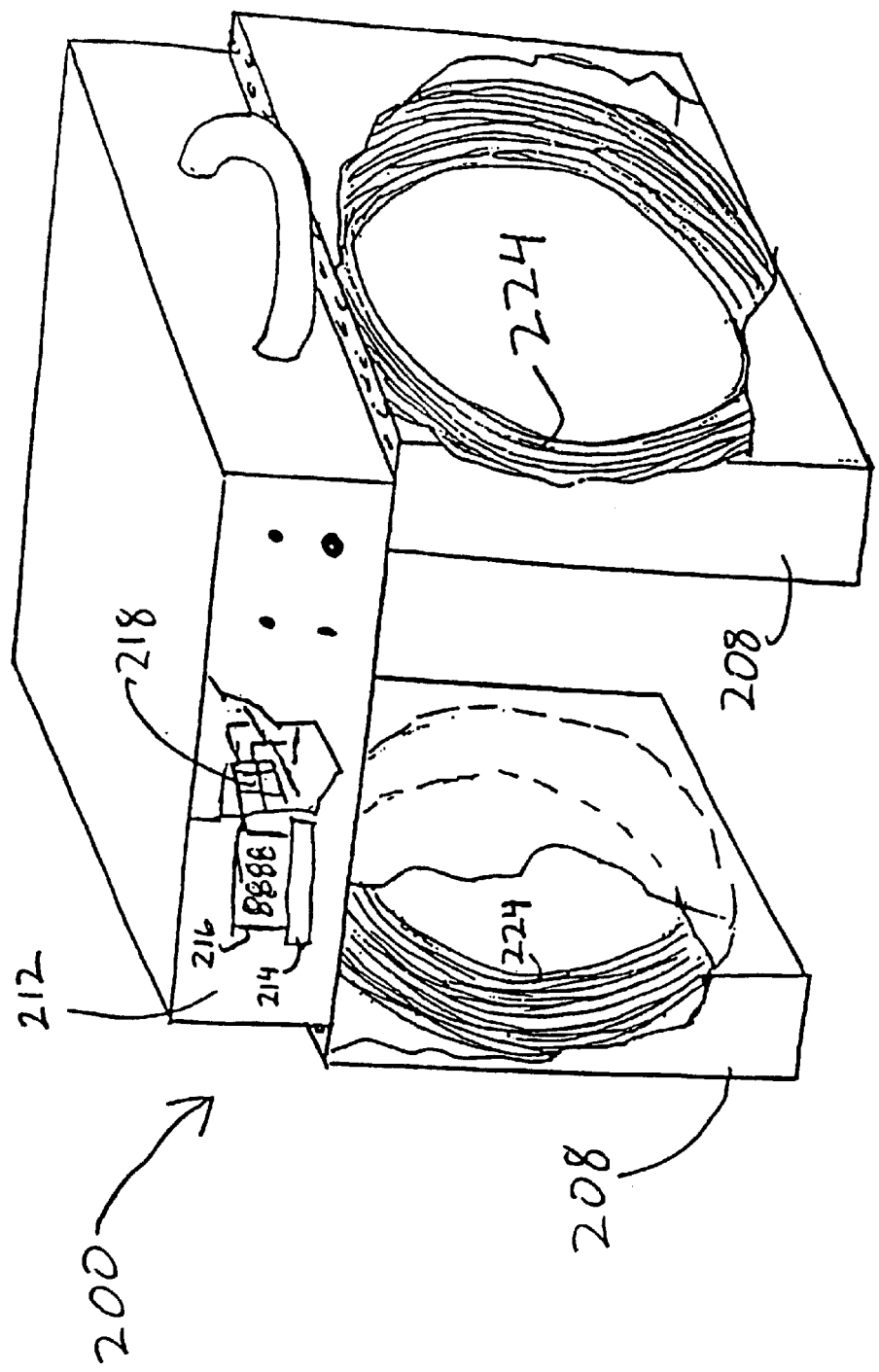

FIG. 20 depicts a perspective and sectional view of the apparatus shown in FIG. 19.

Figure 21:
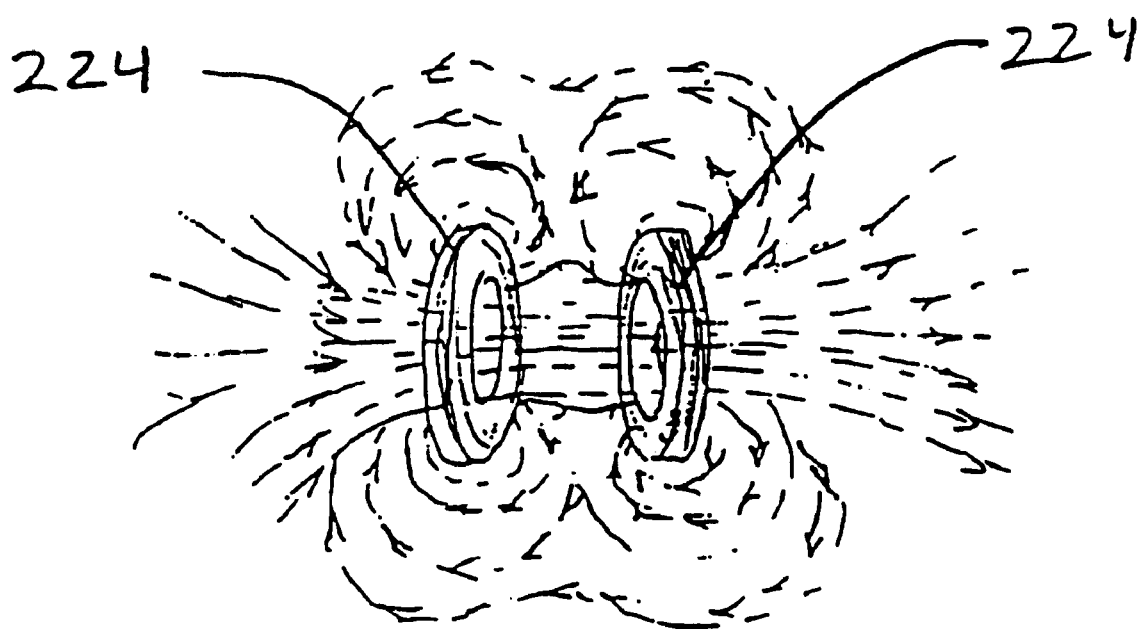

FIG. 21 shows a schematic representation of the electromagnetic flux generated by the time-varying magnetic fields in accordance with this invention.

Figure 22:
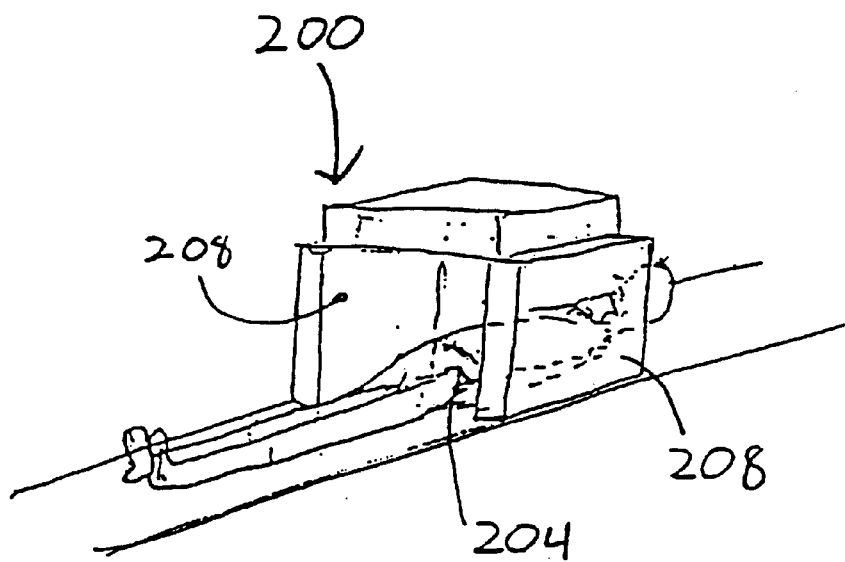

FIG. 22 shows a simplified perspective view of a body extended between the magnetic coils of the apparatus shown in FIG. 19.

Figure 23:
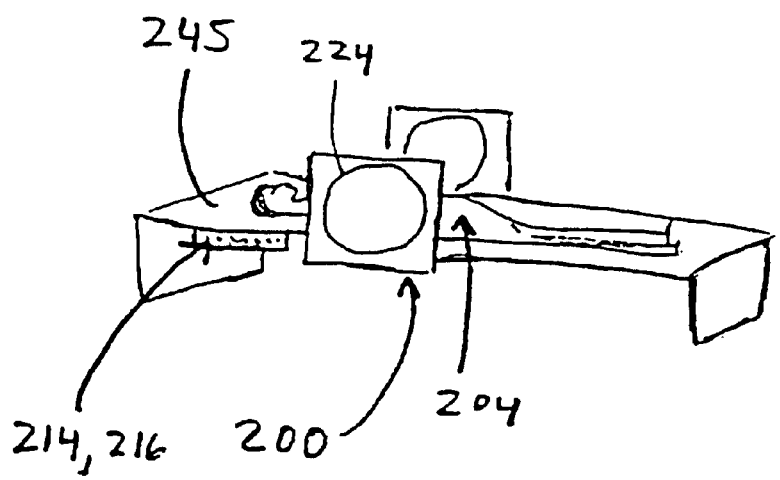

FIG. 23 depicts a simplified perspective view of a body extended between the magnetic coils of the apparatus shown in FIG. 22 wherein the apparatus is placed upside down and is fixed to the bed.

Figure 24:
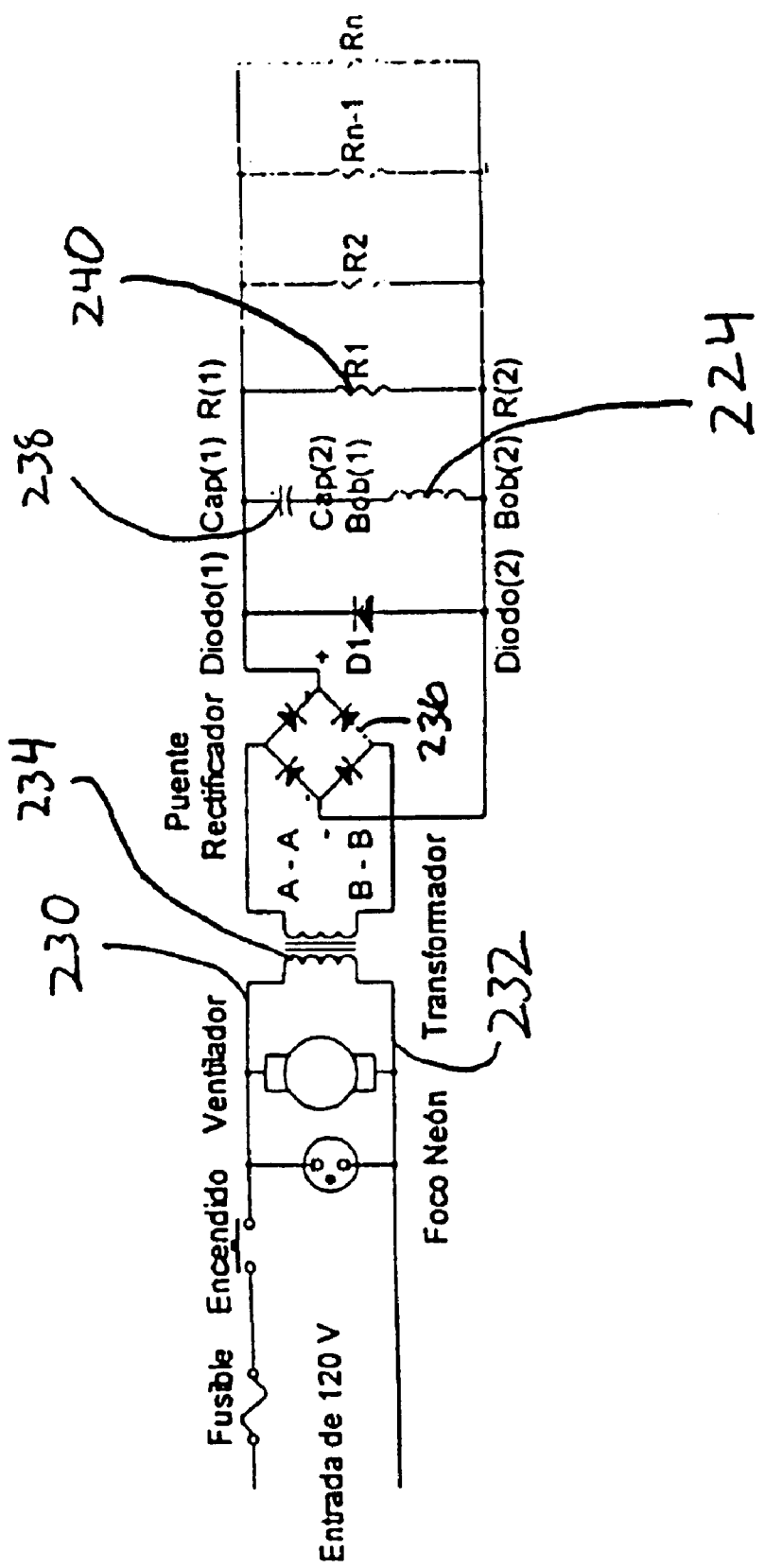

FIG. 24 is a schematic diagram of the electrical power supply circuitry used to energize the magnetic coils of the apparatus of this invention.

The fifth embodiment of the apparatus is shown in FIGS. 25 to 28. In this embodiment, the time-varying magnetic fields of the present invention are generated by coils in a saddle disposition.

Figure 25:
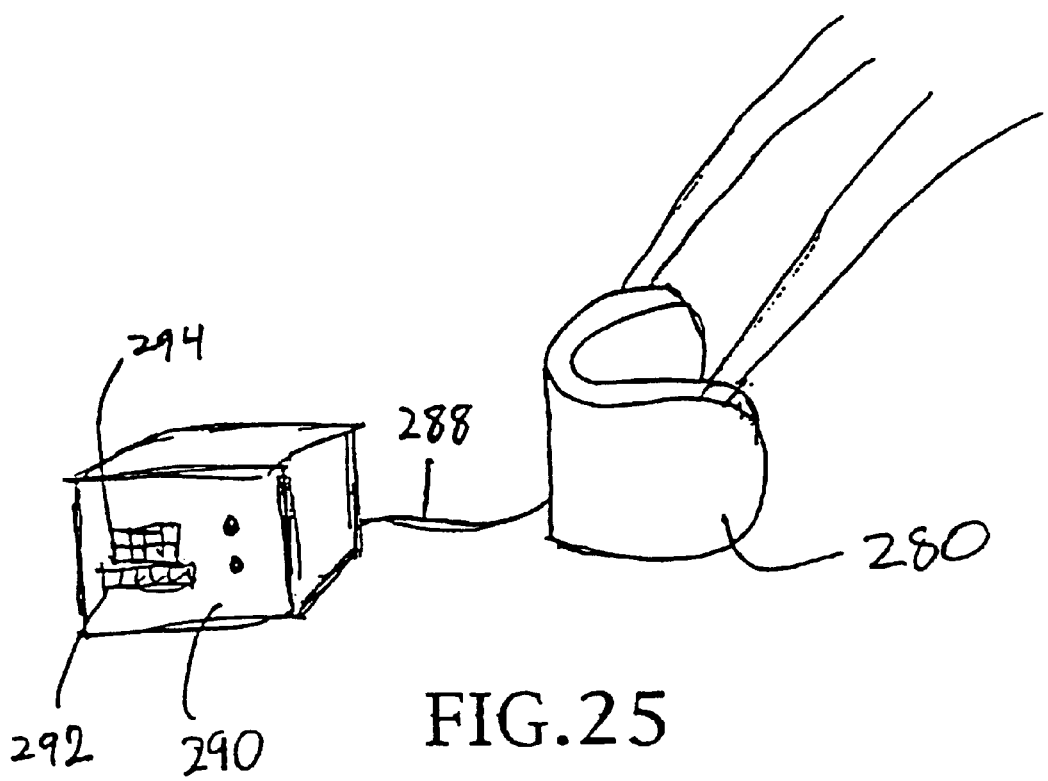

FIG. 25 depicts a simplified perspective view of the apparatus of the present invention as viewed from the outside.

Figure 26:
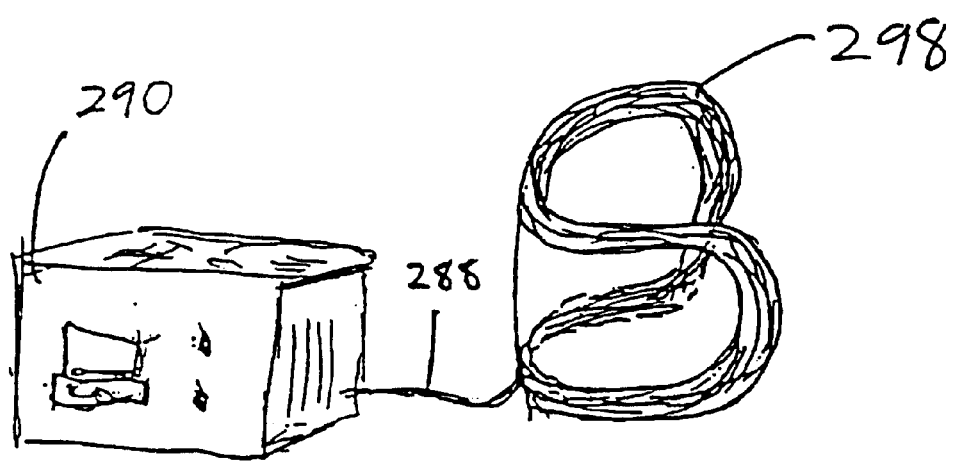

FIG. 26 depicts a partly perspective and sectional view of the apparatus shown in FIG. 25.

Figure 27:
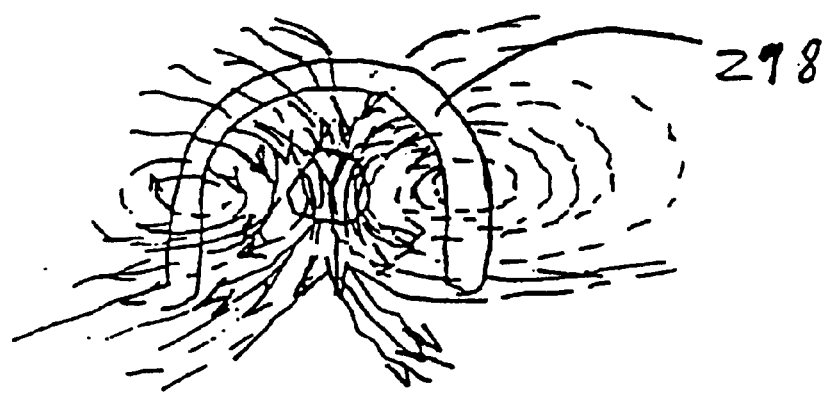

FIG. 27 shows a schematic representation of the electromagnetic flux generated by the time-varying magnetic fields in accordance with this invention.

Figure 28:
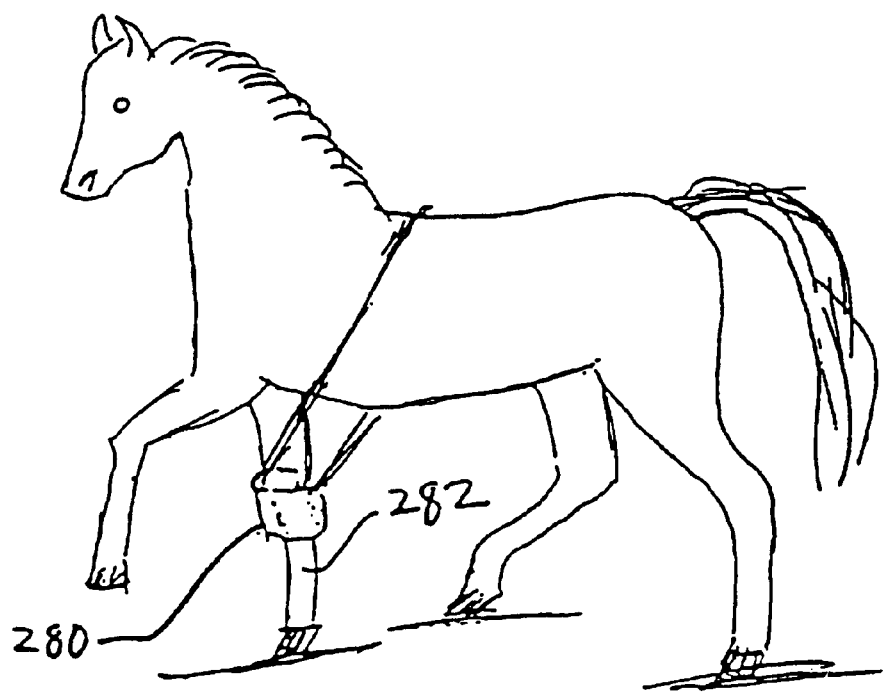

FIG. 28 is a simplified perspective view of a limb of an animal extended between the magnetic coils such as the coils of the apparatus as shown in FIG. 26.

Figure 29:
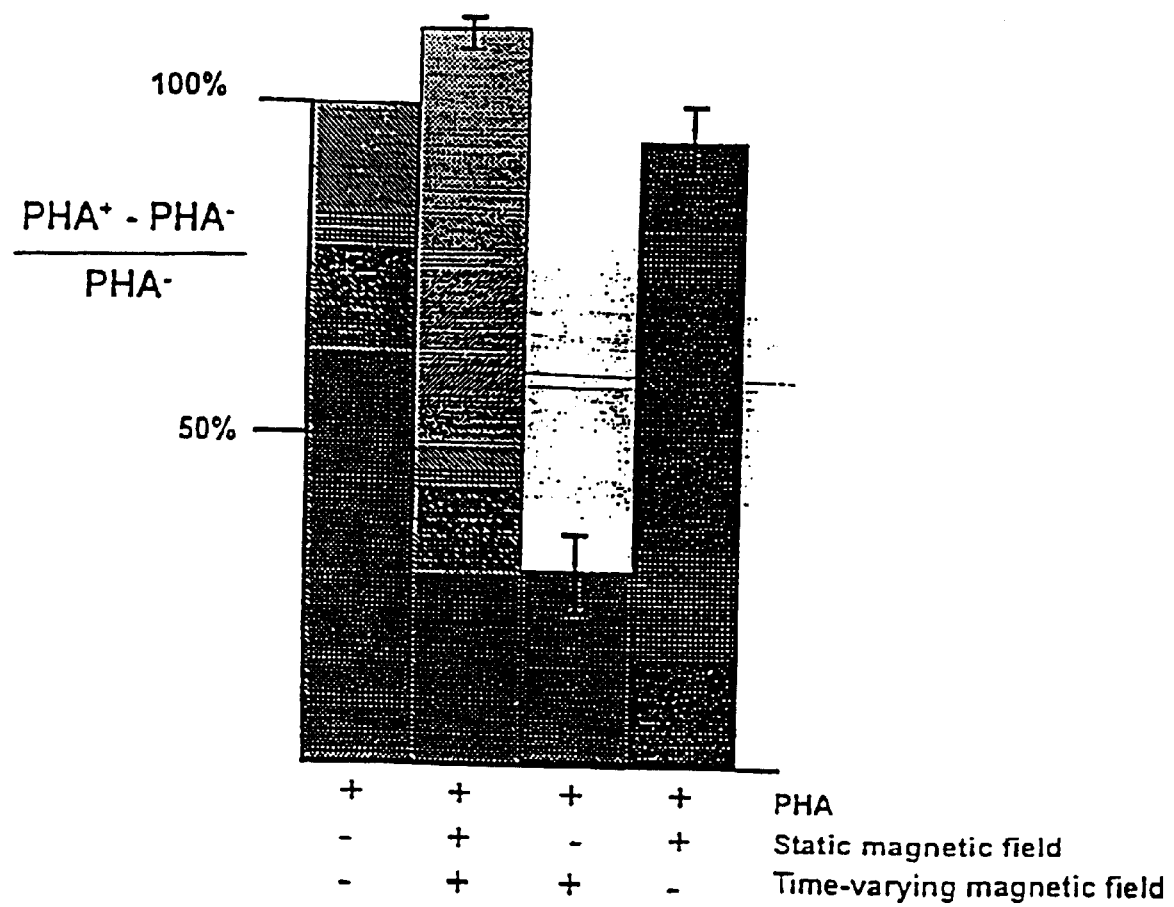

FIG. 29 shows the effect of the magnetic field on the proliferation of peripheral blood mononuclear cells (PBMCs) obtained from normal subjects. The stimulation of PMBCs proliferation by phytohaemaglutinin alone without EMF effect is taken as 100%. The effect of combined static and time-varying magnetic fields produced an 11.1% increase in PBMCs proliferation ($p<0.001$ by Student "T" test). The static magnetic field alone had no statistically significant effect on the proliferation of PBMCs.

The foregoing and other objects and features of the present invention will be more fully appreciated from the following detailed description of the invention and the accompanying drawings.

DETAILED DESCRIPTION OF THE PREFERRED EMBODIMENTS

This invention arose from a desire by the inventor to improve on prior art technology and various somewhat ineffective therapeutic treatments which, in addition, require direct administration to the site of the lesion. This makes them cumbersome, difficult to carry out, and definitely inconvenient to the patient.

The present inventor surprisingly discovered that when a subject with chronic skin lesion(s) and or internal wounds such as bone fracture, partial denervation or viable but underperfused myocardium, is treated by applying an electromagnetic field (EMFs) to a portion of the subject's body in accordance with this invention, the lesions show activated inflammatory reaction and wound repair, and as a result the lesions are drastically and readily reduced, and in many cases readily healed and/or completely eliminated. This is the case even for lesions that are resistant to other generally effective therapies. In viable but underperfused myocardium, the application of EMFs to a portion of the subject's body in accordance with this invention, produce increased collateral circulation and myocardial contraction which are expressed as better clinical improvement. The beneficial results obtained by the inventor are realized by subjecting a site of the subject's body such as a limb, e.g. arm, hand, leg or foot, or even the whole body to the action of specific electromagnetic fields (EMFs) having specific constant and variable components. It is a matter of clinical experience that some subjects with internal and/or external lesions develop resistance to the action of the generally effective wound healing drugs and other therapies upon their administration over a period of time. In addition, other lesions, internal wounds, underperfused tissue, burns and ulcers remain unresponsive to these treatments throughout.

The present inventor has surprisingly found that when such subjects are exposed to external, non-invasive electromagnetic fields (EMFs) in accordance with this invention, they become responsive to previously ineffective treatments, e.g., with known wound healing drugs and other therapies. Many subjects that may benefit from the present treatment have histories of acute myocardial infarction, venous or arterial leg ulcers, burns, pressure ulcers, surgically infected wounds, bone fractures, tissue loss, partial denervation, inadequate blood perfusion and painful inflamed soft tissue, among others, which are resistant or non-responsive to treatment with surgical, pharmacological, or more conventional methods available.

Figure 5:
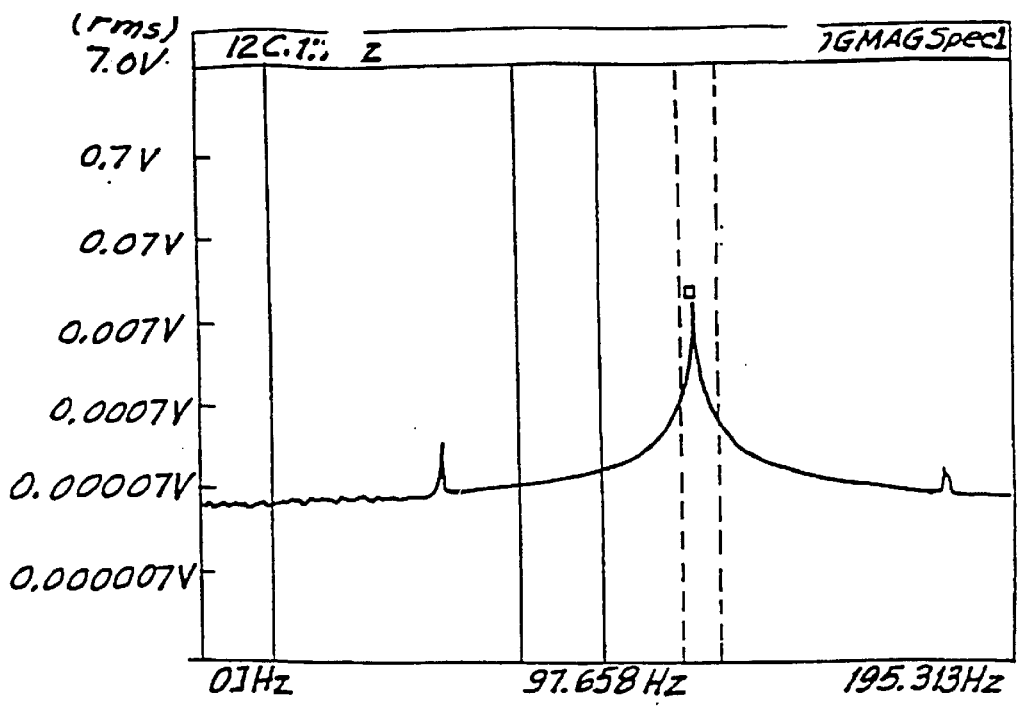
FIG. 5 shows a graphic representation of the frequency distribution of the electromagnetic signals generated by all the embodiments of the apparatus of this invention.

This invention utilizes especially configured electromagnetic fields (EMFs) which may be advantageously applied at a site removed from the wound. The present EMFs stimulate a subject's immune system, including and preferably the subject's activated and memory peripheral blood mononuclear cells (PBMCs), although EMF's action on other EMF's exposed body tissues is not excluded. An activation of the subject's immune system elicits a natural response providing the lesion site and other areas of immune neuroendocrine regulation with the necessary cells, cytokines, angiogenic, osteogenic and neural growth factors, hormones and other immunomodulators which bring about the therapeutic healing of lesions such as burns, venous and arterial leg ulcers, pressure ulcers, chronic infected wounds internal or external areas with inadequate blood perfusion such as viable but underperfused myocardium and the like, muscle loss, bone fractures, partial denervation, painful inflamed soft tissue, and other skin lesions. The electromagnetic fields (EMFs) of this invention comprise time-varying magnetic fields, i.e. alternating currents that oscillate at specified frequencies. In one embodiment of the present invention, the alternating currents are generated in a solenoid with frequencies that range from a few Hertz (more than about 1 cycle per second), about 10 Hertz, about 50 Hertz to about 100 Hertz, about 200 Hertz, about 300 Hertz, with maximum intensities around 120 Hertz and its harmonics. See FIG. 5 of this patent. These time varying magnetic fields have small static magnetic fields associated to them from a few microTeslas, e.g. about 2–5 $\mu$T, about 10 $\mu$T, to about 100 $\mu$T, about 0.3, about 0.8 mT. Strong static magnetic fields with an intensity of about 40, about 50 to about 60 $\mu$T, about 70 $\mu$T, about 80 mT (400 to 800 gauss), are generated by the motion of electrons around atoms and of electrons in crystal lattices within the permanent magnets of this invention placed around the solenoid.

The present method attains healing of a wounded tissue either directly or through immune cells or other exposed tissues or through cell's products, and affords a reduction of pain, edema and infection while restoring or stimulating the subject's immune-mediated signaling network which is necessary to increase angiogenesis, vasculogenesis and wound repair. When a body part such as the arm or the whole body is exposed to the ENTs of this invention, PBMCs as well as other tissues such as the skin, muscle, blood and lymphatic vessels, erythrocytes, bone, nerve and extra cellular matrix, are under the EMFs effects of this invention. Under these conditions the tissues simultaneously exposed, could be stimulated to secrete products that act at a distance in the wound, in the underperfused tissue, in the partially denervated area, in bone fracture healing or in the immune neuroendocrine centers contributing to the regulation of wound repair.

The present invention, thus, relates to a method of treating a body lesion associated with pain, edema, inflammation, bone fractures, partial denervation and/or infection, impaired wound repair and/or underperfused tissue such as viable but underperfused myocardium and the like, inadequate blood perfusion at the site of the lesion, and/or who exhibit an impaired immune-mediated inflammatory response and wound repair process which comprises applying to a subject afflicted with a lesion, externally and non-invasively and at a site removed from the lesion, analgesic, angiogenic, vasculogenic, nerve growth, anti-edema and wound repair effective electromagnetic fields (EMFs) comprising frequencies of a few Hertz, preferably about 0.1 Hz, about 1 Hz, about 5 Hz, about 10 Hz, about 20 Hz, about 60 Hz, about 80 Hz, about 100 Hz, about 120 Hz to less than about 180 Hz, about 240 Hz, about 300 Hz, and static magnetic field components having a minimum intensity of a few microTesla, e.g. about 2–4 $\mu$T, about 10 $\mu$T, about 50 $\mu$T, about 100 $\mu$T to about 0.3, about 0.4, about 0.5, about 0.6, about 0.7, about 0.8 mT. These EMFs may be used alone or in combination with a static magnetic field of about 40, about 50 to about 70, about 80 mT (or about 400, about 450, about 500, about 550 Gauss to about 600, about 650, about 700, about 800 Gauss).

In the method of invention, the EMFs may be applied to a limb of the subject, that is to an arm or a leg, and in some instances to a hand or a foot, to other parts of the subject's body, or to the whole body. The present method may be conducted for various periods of time, including about 5 minutes to about 7 hours per administration. In one preferred embodiment, the electromagnetic fields (EMFs) administration is conducted over a period of time effective to expose the subject's entire blood volume at least once to the EMFs. This procedure ensures that the entire blood volume is exposed to the EMFs and the inductive effect imparted to all cells present in the blood stream, particularly activated and memory peripheral blood mononuclear cells, and their progenitor cells. Although in many cases, one application of the electromagnetic fields (EMFs) may suffice, the application may be repeated as many times as necessary. Preferably once a week, twice a week, 3, 4, 5, 6, and 7 times a week and up to about 1, 2, 3, 4, 5, 6, 7 and 8 weeks, and even several months and years. In addition, the method also includes the periodic reapplication of EMFs.

The method of this invention may be applied to the treatment of diseases and conditions associated with and/or caused by, and/or resulting in, a body lesion(s). In all cases, a sufficient number of applications of the electromagnetic fields (EMFs) maybe delivered until the lesion is alleviated and/or fully healed. Among the lesions that may be treated with the present technology are chronic wounds, partial denervation, loss of muscular tissue, bone fractures, burns, lesions caused by inadequate blood perfusion, such as viable but underperfused myocardium and the like, consequences of unsuccessful surgery, and different types of venous, arterial and vascular problems, including arterial and venous ulcers. Examples of various lesions and their descriptions are provided below as well as the various other treatments presently available and their degree or lack of success in overcoming the diseases and conditions.

Chronic Venous and Arterial Leg Ulcers

I. Chronic Venous Leg Ulcers

Initially, chronic venous leg ulcers are generally caused by venous insufficiency and valve incompetence that lead to increased ambulatory pressure. This effect extends, in most cases to small veins, venules and capillaries. The pressure results in augmented interendothelial spaces, which, in turn, enhance extravasion of small solutes, macromolecules and blood cells. This is seen as a leakage of small and large molecules as well as blood cells out of the endothelial tissues and into the interstitial space. Concurrent with this, lymphoangiopathy and reduced lymphatic drainage are seen, which result in fall clinical edema. Slow blood flow develops and increased adherence of white blood cells and platelets to endothelium leads to the formation of microthrombi which reduce the number of capillaries present. These changes ultimately lead to necrosis, which is substituted by fibrous tissue, which predispose the skin of the gaiter area to ulceration.

I.1 Venous Leg Ulcers Treatment

Most macrovascular alterations may be conservatively treated by leg-elevation, external graduated compression and/or surgical procedures. Microvascular changes are targeted by means of systemic pharmacological treatment with, for example, venotonic drugs, platelet aggregation inhibitors, white blood cells activation inhibitors and fibrinolytic and thrombolytic agents, which are among the most commonly prescribed medicines. However at present no convincing evidence exists to recommend these agents in venous leg ulcer treatment.

II. Chronic Arterial Leg Ulcers

In most cases, atherosclerosis of the lower limbs is the first cause of arterial leg ulcers and it leads to a progressive narrowing of the arterial lumen and a gradual reduction of blood flow to the distal circulation. As the disease progresses, the atherosclerotic lesions generally extend. When the blood flow becomes sufficiently reduced and the perfusion pressure of nutritional capillaries uneven, insufficient nutritional support of peripheral microcirculation ensues. In addition, an increase in leukocyte adhesion, platelet aggregation, rheological alterations and arteriolar microthrombi are observed. These contribute to further reducing the number of perused capillaries. The described arterial alterations are expressed clinically as rest pain, throphic skin changes and ulceration. In addition, these lesions often get infected.

II.1 Chronic Arterial Leg Ulcer Treatment

Present invasive treatments include angioplasty, vascular reconstruction and amputation. Most pharmacological treatments are focused to reduce pain, and to reduce infection. At present the European Consensus for Critical Leg Ischemia does not recommend any additional pharmacological treatment for arterial leg ulcers.

III. Pressure Ulcers (Decubitus Ulcers)

Most pressure ulcers are commonly produced as a consequence and a complication of immobility. In many instances, they are resistant to medical treatment. This resistance is greatly increased by malnutrition, infections and old age. These ulcers generally increase the risk of death of patients that remain for extended periods in acute care hospitals and nursing homes. In spinal cord injured patients, for example, his problem accounts for 7–8% of deaths. Although pressure, friction, shearing forces and moisture have been implicated in the pathogenesis of skin breakdown, the process may be also aggravated by secondary infection.

III.1 Pressure Ulcer (Decubitus Ulcers) Treatment

A most common treatment starts with the repositioning of the patient to avoid prolonged pressure in any specific area of the body. In addition to this, the basic treatment procedures commonly applied to these patients are general wound care and treatments aimed to control the basic disease. The patients are also advised on adequate nutritional habits and recommended to take supplements of ascorbic acid, zinc, and selenium.

IV. Chronic Wounds

In most cases of chronic wounds, inadequate nutritious blood supply, edema, tissue anoxia, cell death and infection, reinforced by aging and sustained stress, reduce peptide signaling among cells involving growth factors, hormones and the like as well as their effects in the immune-neuroendocrine communication network. Healing is impaired due to the absence of a normal immune-mediated inflammatory response and/or repair process. The presently available treatments are only partially effective and the long-term prognosis is poor for these patients. The present status emphasizes the need of new methods to treat chronic wounds such as activating the cell's and cytokine's signaling language necessary for wound repair, nerve growth, vasculogenesis and angiogenesis.

V. Myocardial Infarction

Atherosclerosis is a generalized disease responsible for occlusive arterial disease such as lower-limb arterial disease (chronic arterial leg ulcers), myocardial infarction and stroke. The etiologic factors (arterial hypertension, high serum cholesterol, smoking, stress, diabetes mellitus) are similar in these diseases. Most deaths in patients with myocardial infarction are caused by arrythmias, infarct expansion and post-infarction remodeling.

V.1 Myocardial Infarction Treatment

Preventive measurements are focused to eliminate or control the etiological factors. Reduction of early mortality of myocardial infarction can be achieved by the use of B-blockers, thrombolytic therapy followed by catheter based revascularization, angioplasty with or without stenting, by-pass surgery, angiotensin converting enzyme inhibitors and aspirin. To those patients with viable but underperfused myocardium who are not candidates for coronary revascularization, angiogenic growth factors are a novel approach still under clinical investigation.

VI. Bone Fractures

In bone fractures, three overlapping phases of fracture healing have been described: a) the inflammatory phase which is similar to the inflammatory stage of a skin wound, b) the reparative phase in which osteoblast proliferation and endosteal tissues are central for callus formation, and c) the remodeling phase, where the fracture callus and bone are remodeled to restore normal shape and strength. In the three phases of fracture healing PBMCs and cytokines play a central role. Current treatment includes surgery, fixation and locally applied electromagnetic fields to induce osteogenesis.

VII. Spinal Muscular Athrophies

The spinal muscular athrophies of infancy and childhood are diseases in which there is a progressive degeneration of the motor neurons of the spinal cord, with early age of onset and genetic determination. Although clinically resembling muscular dystrophies, in these patients the muscular atrophy is secondary to nerve degeneration. Some infants develop normally for several months before weakness become apparent. The trunk, pelvic and shoulder girdle muscle groups are disproportionally affected. The disease runs a steadily downhill course, and most patients have a short period of life. A few may survive for several years, and even are able to work with support. At the present time there is no cure for these diseases. Treatment is restricted to rehabilitation therapy and orthopaedic support. New approaches to nerve regeneration are neurothophic factors, Schwann cells manipulation, and locally applied electric currents or electromagnetic fields to induce electric currents, although these treatments are not used to treat spinal muscular atrophies.

Types of diseases and conditions which are normally associated with body lesions are, for example, partial denervation, tissue loss, burns, bone fractures, ischemic and traumatic lesions, chronic wounds and ulcers. By means of more specific examples, the following diseases and conditions have been observed to fall in the above described categories: diseases and conditions accompanied by inadequate blood perfusion such as viable but underperfused myocardium and the like, tissue necrosis, pain, edema and infection, such as internal and external chronic wounds, produced by atherosclerosis, arterial hypertension, diabetes, vasculitis, venous insufficiency, varicose veins, deep vein thrombosis, rheumatoid arthritis, prolonged immobility obesity, vascular necrosis, chronic wounds and aggravated burns, lesions produced by trauma, burns and surgery. The present treatment is particularly suitable for application to conditions where nutritious blood supply and tissue regeneration is needed such as skin, muscle, nerve and connective tissue including, but not limited to viable but underperfused myocardium, ulcers such as venous ulcers, arterial ulcers, decubitus ulcers, deep pressure ulcers, medial malleolus ulcers, factitial ulcers, ulcers produced by trauma and surgery and lower limb ulcers, spinal muscle atrophy, among others. The lower limb ulcers are individually or collectively located on different areas of the subject's leg or foot. Wounds that are treatable with the present method are of surgical or non-surgical origin. Common non-surgical wounds are viable but underperfused myocardium, chronic venous and arterial leg ulcers, pressure ulcers and the like and common surgical wounds are wounds associated with or caused by surgery, silicon implants or by a surgical drainage. Typical diseases and conditions associated with or causing inadequate blood perfusion, are for example: atherosclerosis, venous insufficiency, deep vein thrombosis venous and arterial hypertension, vasculitis, diabetes, rheumatoid arthritis, obesity, and diseases associated with long periods of inactivity, such as those occurring when a subject sits or lies down for an extended period of time.

The present method is also suitable for increasing the effect of a treatment applied to a body lesion associated with pain, edema and/or inflammation. In many cases, a patient on whom a treatment was previously ineffective is made to respond to the same treatment upon a series of electromagnetic fields (EMFs) applications. The present method does, in this manner, increase the subject responsiveness to the treatment, which, in turn, results in alleviation of the body lesion and the pain, edema and/or inflammation accompanying it.

The present method is of particular value where a subject had become resistant to the agent for treating the disorder or condition, and the application of the electromagnetic fields (EMFs) restores the ability of pharmaceutical or surgical treatments to improve the subject's health and mobility. Examples of such treatments are angioplasty, surgery, saphenectomy, skin grafts, wound closure, stitching, bandaging, anti-hypertensive therapy, pharmaceutical composition administration, nursing care and body lesion clean up, among others. Examples of pharmaceutical compositions which are typically administered to patients afflicted with the sort of lesions described above are pain killers, anti-inflammatory agents, antibiotics, flavinoids, tissue plasminogen activator, aspirin, prostacyclin analogs, prostanoids, venotonic drugs, fibrinolytic and thrombolytic agent, diets and the like. These agents may also be administered in conjunction with or subsequent to the administration of EMFs in accordance with this invention.

The preferred embodiments of the invention will now be described with reference to the drawings in so far as this may facilitate the understanding of this invention. The present treatment may be applied with the apparatus of the invention exemplarily illustrated in FIGS. 1–2, 8–9, 10–11, 14–15, 17–18, 19–20, 22–23 and 25–26. The designs of the various embodiments of the present apparatus are derived from observations made in patients with similar problems that were exposed to time-varying magnetic fields of this invention, either alone, or in combination, with static magnetic fields, FIGS. 1–9 illustrate the use of time-varying magnetic fields in combination with static magnetic fields. FIGS. 8 and 9 illustrate an enlarged embodiment of this invention which has a large enough internal chamber to expose a large part of part of a human body such as the torso.

In particularly preferred embodiments of the apparatus used many times with success, the permanent magnets are eliminated but the time-varying electromagnetic fields are maintained. See, FIGS. 10 to 16. Another embodiment provides an apparatus similar to the one previously described but equipped with a large enough internal chamber to expose a part of the human body, e.g. from the upper limit of the aorta to the lower limit of the liver and spleen, inside the chamber to the magnetic field. See, FIGS. 17 and 18. In this manner time-varying magnetic fields of the same characteristics can be applied to the patient's large blood and lymph vessels: aorta, vana cava and thoracic duct, as well as to the large blood and lymph reservoirs: heart, lung, liver, spleen, and paravertebral ganglia. This treatment simultaneously exposes large numbers of peripheral blood mononuclear cells to the electromagnetic fields, and reduces treatment time. These embodiments of the apparatus were designed to provide a comfortable position for the patient during exposure to the magnetic fields.

In still another embodiment of the apparatus of the invention, the characteristics of the time-varying magnetic fields are the same as in the above-described apparatus but are generated by, for example, two parallel coils, i.e. Hemholtz coils. The coils produce homogeneous electromagnetic fields in the center between them. This embodiment can be used to expose part of the human body lying on a bed to the time varying magnetic fields. See, FIGS. 19–22.

Yet another embodiment provides a slight variation of the apparatus described above, but where similar equipment is placed upside down and fixed-to the sides of a narrow bed made of non magnetic material. The magnetic flux produced by the coils now runs perpendicular to the body axis. The controls may be easily located at bedside, as shown. See, FIG. 23.

Another embodiment of the present apparatus is provided with coils arranged in a saddle disposition so the magnetic fields run perpendicular to the limb. This equipment was built for veterinary applications and has been successfully used to cure an inflamed joint and skin wound of a horse. However, it may also be used in humans. See, FIGS. 25 to 28.

In still two farther embodiments of the invention, the electromagnetic fields of his invention may be generated in two different manners. One manner is where the electromagnetic fields are generated by modulating continuous about 27.12 Mhz waves that transport electrical and magnetic energy through space (transport wave) at the same or similar frequencies of the present invention (i.e.: an antenna to focus the electromagnetic fields of the present invention in any direction). The other way is by modulating electromagnetic fields of high intensity and frequency (transporting waves) such as those electromagnetic fields produced by a Tesla coil, to the same or similar frequencies as employed in the present invention. In the latter case, the electromagnetic fields traveling through space may reach a patient lying in bed or seated without being attached to the apparatus.

With reference to FIGS. 1 and 2, an embodiment of the apparatus of the present invention may be in the general form of a rectangular or square box 101, which may be fabricated from wood, plastic or other non-magnetic material to prevent interference with the application of an electromagnetic field to a patient's body part. The front or face panel 103 of the apparatus may have generally a circular opening 104 which extends as a elongated annular passageway 105 in the box 101. The passageway 105 generally extends horizontally inside the box 101, and when not in use, it may be closed and has an end 109 at the rear wall or panel 111. Preferably installed on the face panel 103 are a timer 113 and a control mechanism 115, both of which are connected to an electronic panel 117, for varying and controlling the intensity and duration of the magnetic field (s).

Figure 6:
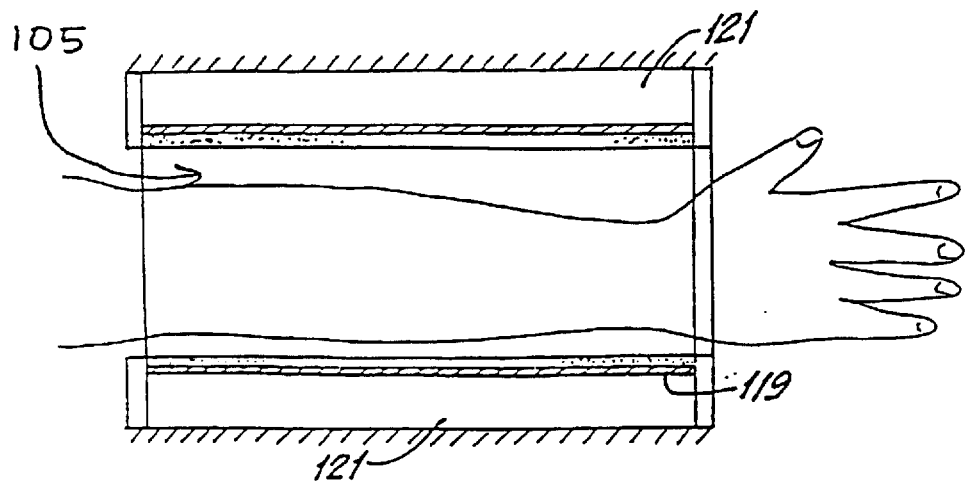
FIG. 6 is a simplified schematic top view of an arm extended inside the solenoid and the permanent magnets such as those shown in FIG. 2.
Figure 7:
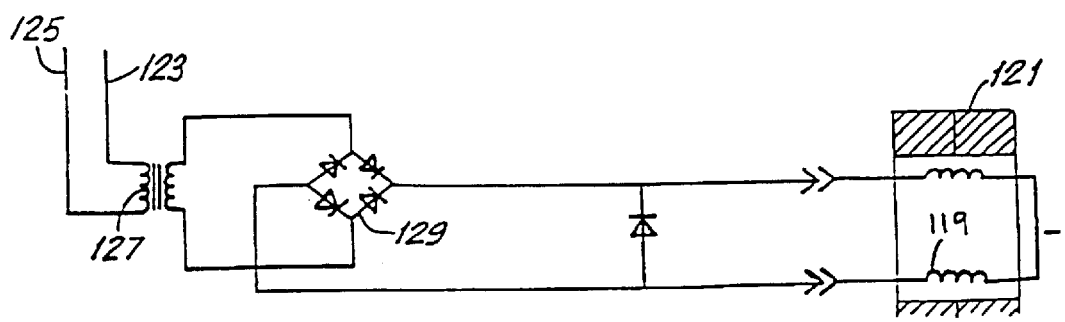
FIG. 7 is a schematic diagram of the electrical power supply circuitry used to energize the solenoid of the apparatuses of this invention.

As shown in FIG. 6, disposed on each interior longitudinal side of the passageway 105 is a solenoid coil 119 for supplying a time-varying magnetic field. In addition, FIG. 6 shows the permanent magnets 121 for supplying the static magnetic field. Referring to FIG. 7, an electric current is supplied from an AC power source (not shown) through power lines 123, 125, and into a transformer 127 and a rectifier bridge 129 to the magnetic coil 119. The manner and details for supplying electric current to the solenoid are well known in the art, and are not per se critical in this invention.

With reference to FIGS. 8 and 9, another embodiment provides an apparatus similar to the one described in the previous paragraph. This embodiment is an enlarged version of the embodiment shown in FIGS. 1 to 7. This second embodiment allows exposure to a part or the whole body to the EMFs as shown in FIGS. 8 and 9. In this design, the major blood vessels (aorta, cava veins) thoracic duct, paravertebral lymph nodes and major blood reservoirs (liver, spleen, lung and heart) can be exposed simultaneously to the combination of time-varying magnetic fields and static magnetic fields (not shown), reducing the patient exposure time.

This apparatus has a circular shaped housing 130 contain the coil 119 and strong permanent magnets 121. The circular shaped housing 130 has an internal chamber 132 large enough to expose part of the body of a patient 134 to the magnetic field. The housing 130 may be fixed to a narrow bed 136 made of non-magnetic material. The timer 113 and control mechanism 115 connected to an electronic panel, as in the previous embodiment, may be located at the side of the bed. Preferably, the housing is made from a non-magnetic material such as wood or plastic.

In another embodiment shown in FIGS. 10 and 11, the identical apparatus of the embodiment of FIGS. 1 and 2 is used without the permanent magnets 121. As shown in FIG. 13, this embodiment also includes a coil support 250 for supporting the coil 119 and a tube wall 252.

In another embodiment, shown in FIGS. 14 to 16, which is a simplified version of the previous embodiment shown in FIGS. 10 to 13, a solenoid, such as a magnetic coil 157, is mounted within a cylindrically shaped housing 158. The cylindrically shaped housing 158 includes an elongated annular passage 159 formed therethrough. The magnetic coil 157 is disposed within the cylindrically shaped housing 158 and around the annular passage 159. The housing and the annular passage are sized to comfortably accommodate the limb of a patient, such as the forearm 160 or upper arm 162 of a patient, allowing more mobility to the patient while being exposed to the EMFs.

Therefore, this design permits comfortable and mobile limb exposure to the ENVs of the invention. Preferably, the cylindrically shaped housing is made of a light non-magnetic material. Such non-magnetic materials include plastic or wood. Also, the transformer 127 and rectifier bridge 129 (shown in FIG. 7), along with a pair of contacts 152 which are connectable to a power source, are contained within a small adapter box 150, to readily obtain electric current from an AC power source (not shown). The adapter box 150 with the contacts, the transformer, and the rectifier bridge contained therein, is connected to the coil 157 by two long cables 154 which provide current to the coil 157.

With reference to FIGS. 17 and 18, another embodiment provides an apparatus similar to the embodiment shown in FIGS. 10 to 13. This embodiment is an enlarged version of the embodiment shown in FIGS. 10 to 13. This embodiment allows a part or the whole body to be exposed to the EMFs as shown in FIGS. 17 and 18. In this design the major blood vessels (aorta and cava veins) thoracic duct, paravertebral lymph nodes and major blood reservoirs (liver, spleen, lung and heart) can be exposed simultaneously to EMFs (not shown), reducing the patient exposure time. This apparatus has a circular shaped housing 260 containing the coil 119 and includes an internal chamber 262 large enough to expose part of the body of a patient 204 to the magnetic field. The housing 260 may be fixed to a narrow bed 245 made of non-magnetic material. The timer 113 and the control mechanism 115 connected to an electronic panel, may be located at the side of the bed. Preferably, the housing is made from a non-magnetic material such as wood or plastic.

A magnetic field may also be applied with another embodiment illustrated in FIGS. 19 and 20. This apparatus may be in the general form of a U-shaped housing 200. Referring to FIG. 22, part of the body of a patient 204 may be exposed to a homogeneous electromagnetic field in accordance with this invention between the lateral walls 208 of the housing 200 of the apparatus. The apparatus may be fabricated from wood, plastic, or other non-magnetic material, to prevent interference with the application of an electromagnetic field to a patient's body part. With reference again to FIG. 19, installed on the face panel 212 are a timer 214 and a control mechanism 216, both of which are connected to an electronic panel 218 shown in FIG. 20, for varying and controlling the intensity and duration of the electromagnetic field(s).

As shown in FIG. 20 disposed on each interior of the lateral walls 208 is a coil 224 for supplying time-varying magnetic fields. The lateral walls serve as supports to maintain the coils in a Hemholtz disposition. FIG. 21 shows a schematic representation of the electromagnetic flux generated by the opposed Hemholtz coils 224. Referring to FIG. 24, an electric current is supplied from an AC power source (not shown) through power lines 230, 232 and into a transformer 234 and a rectifier bridge 236. To reduce heating of the coils by the current, a capacitor 238, and resistors 240 are used to reduce the effective current to the magnetic coils 224. A fan is used to cool the resistors. The manner and details for supplying electric current to the coils are well known in the art, and are not per se critical in this invention.

A slight variation of this embodiment is shown in FIG. 23. In this embodiment, similar equipment is used, but the housing 200 is turned upside down and fixed to the sides of a narrow bed 245 made of non-magnetic material. The magnetic flux produced by the coils now runs perpendicular to the axis of the body 204. The timer and control mechanism 214 and 216 may be easily located at the side of the bed.

Another embodiment of the apparatus of this invention is illustrated in FIGS. 25 and 26. The apparatus may be in the general form of a saddle 280. Referring to FIG. 28, the saddle may be placed on a limb or a body part 282 to expose a patient to the homogeneous electromagnetic field in accordance with this invention. The apparatus may be fabricated from wood, plastic or other non-magnetic material to prevent interference with the application of an electromagnetic field to a patient's body part. As shown in FIGS. 25 and 26, the saddle is connected through electric cables 288 to the control unit 290 which contains a timer 292 and a control mechanism 294, both of which are connected to an electronic panel (not shown) for varying and controlling the intensity and duration of the electromagnetic field(s).

As shown in FIG. 26 disposed on the interior of the saddle walls are the coils 298 for supplying the time-varying magnetic field. Referring to FIG. 24, the same circuit as used in the previous embodiment, FIGS. 19 to 23, can be used to deliver current to the coils 298 of the current embodiment illustrated in FIGS. 25 to 28. An electric current is supplied from an AC power source (not shown) through power lines 230, 232 and into the transformer 234 and the rectifier bridge 236. To prevent heating of the coils by the current, a capacitor 238, and resistors 240 are used to reduce the effective current to the magnetic coils 298 and a fan is used to cool the resistors. The manner and details for supplying electric current to the coils are well known in the art, and are not per se critical in this invention.

There are two additional ways in which the electromagnetic fields of this invention may be generated. One is by modulating a continuous 27.12 MHz waves that transport electrical and magnetic energy through space (transporting waves) at the same frequencies of the present invention (i.e. an antenna to focus the electromagnetic fields of the present invention in any direction), and the other by modulating to the same frequencies of the present invention the electromagnetic fields of high intensity and frequency produced by a Tesla coil, (transporting waves). The electromagnetic fields of this last design travel through space so a patient lying in bed or seated to a nearby source may be treated without seeing the apparatus.

Figure 3:
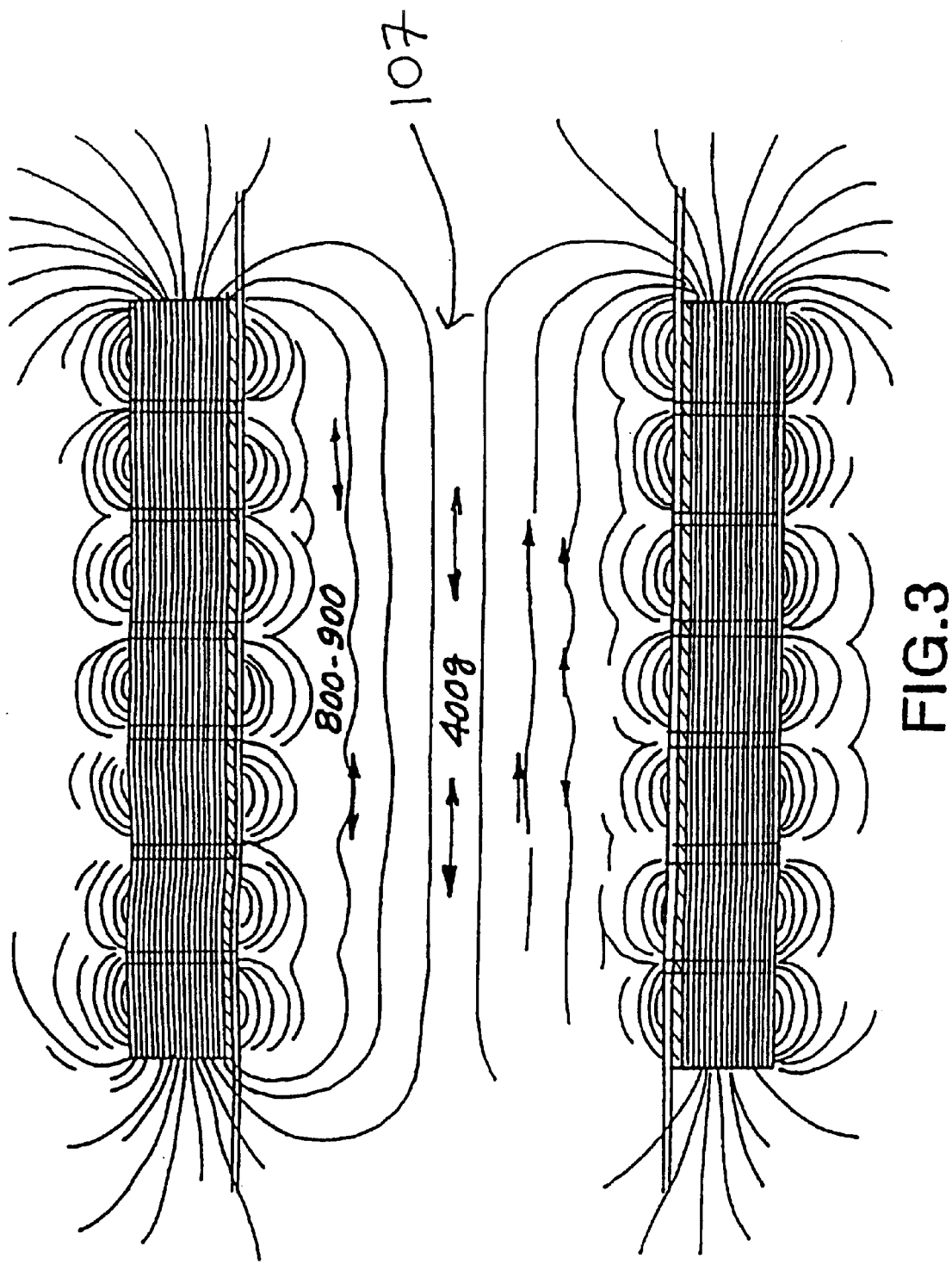
FIG. 3 shows a schematic representation of the magnetic flux generated by the combined variable and static magnetic fields generated in accordance with this invention.
Figure 4:
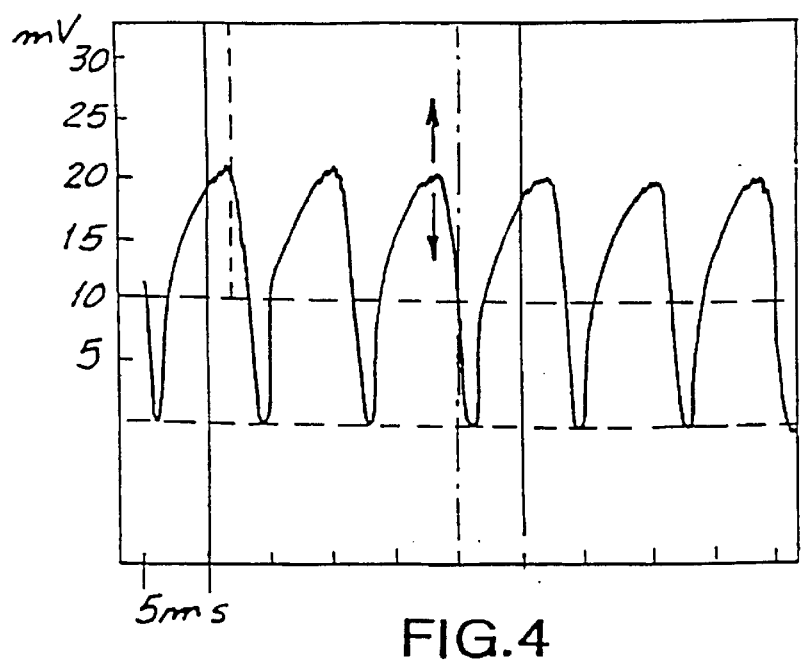
FIG. 4 shows a graphic representation of the waveform generated by the electric current supplied to the coils by the electrical circuit in all the embodiments of the apparatus of this invention.

In order to treat a patient afflicted with skin lesions or internal wounds in accordance with the method of this invention, the patient's limb (e.g. a hand or part of an arm) may be simply inserted through the opening 104, and partly extended through the passageway 105. The power source is then turned on to supply an electric current to the solenoid coil 119. The lines of flux produced by the magnetic fields generated within the space 107 are shown in FIG. 3, and are seen to comprise variable as well as static magnetic flux lines. It has been found that the treatment is most effective when the electromagnetic field is applied at extremely low frequencies of more than one Hertz to less than about 300 Hz. The frequencies spectral content of the time-varying magnetic field are higher around approximately 120 Hz and its harmonics. See, for example FIG. 5. These frequencies have a static magnetic field component with an intensity of about 0.3 to about 0.8 mT root mean square (rms) and these EMFs can be used alone or in combination with a homogeneous static magnetic field of about 40 to about 80 mT (about 400 to about 800 Gauss). Thus, there are two static magnetic fields: one is generated jointly with the time-varying magnetic field and preferably has a low magnetic flux density of a few microteslas to a maximum of about 0.3 to about 0.8 mT (rms) and the second has a higher density and is provided by the permanent magnets with a magnetic flux density of about 40 to about 80 mT, which is equivalent to about 400 to about 800 Gauss. The relationship between the instantaneous current supplied by the electric circuit to the magnetic coils as a function of time are shown as a series of waves in the forms shown in FIG. 4. As previously indicated, the application of time-varying magnetic fields with frequencies of a few Hertz (more than one) to less than about 300 Hz and static magnetic field components having an intensity of about 0.3 to about 0.8 mT used alone or with the simultaneous application of an homogeneous static magnetic field of about 40 to 80 mT or about 400 to about 800 Gauss, constitutes an essential (critical) feature of the method of this invention.

The wound healing effects of the present method and apparatus which were observed in patients are obtained by applying the time-varying electromagnetic fields described herein, either alone or in combination with static electromagnetic fields. Generally, however, each component separately and their combination evidence different degrees of effect on the proliferation of peripheral blood mononuclear cells (PBMCs). This may be seen clearly in FIG. 29, which shows the different degree of effects on cell proliferation evidenced by different types of magnetic fields when applied to PBMCs obtained from normal subjects (the 100% cell proliferation control are PBMCs stimulated to proliferate with phytohaemaglutinin without the presence of any of the magnetic fields (EMFs) of this invention). The application of a combination of static and time-varying fields produced a 11.1% increase of PBMCs proliferation (P< 0.001 Student "T" test), the application of time-varying magnetic field alone produced a 67% reduction of PBMCs proliferation (P< 0.001 Student "T" test), and the application of a static magnetic field alone had no significant effect on PBMCs proliferation.

For maximum benefit from the treatment, the magnetic fields are preferably applied to the patient's limb for about several minutes to about eight hours. The preferred exposure time was calculated so that a blood volume equivalent to the patient's entire blood volume is exposed to the magnetic field at least once. The exposure frequency may be varied from a maximum of about 30 minutes to about seven hours a day, to a minimum of about 30 minutes a week, depending on the observed lesion repair and wound healing observed.

The effect of EMFs in accordance with the present invention applied on isolated peripheral blood mononuclear cells (PBMCs) to modulate their proliferation patterns, their systemic effects in vivo and the application of external time-varying magnetic fields alone or in combination with static variable magnetic field for treatment of patients with chronic skin ulcers, chronic wounds, viable but underperfused myocardium, bone fractures and partial denervation is illustrated in the following examples.

The following examples illustrate the effectiveness of the method of this invention. These examples, however, are merely illustrative of the invention and are not to be construed so as to limit the scope thereof.

EXAMPLES

In Vitro Effect

The following experiments show the effect of electromagnetic fields (EMFs), applied in accordance with the present invention, on the peripheral blood mononuclear cells (PBMCs).

Example 1

In Vitro Effects of Different Electromagnetic Fields on PBMC Proliferation

Peripheral blood mononuclear cells (PBMCs) were obtained by venous puncture and fractionated on a ficoll gradient. The fraction contain PBMCs was washed 3 times and resuspended in phosphate buffered saline to a final concentration of $5 \times 10^6$ cells/ml. PBMCs aliquots 0.2 ml aliquots of $5 \times 10^6$ cells/ml, plus 1 $\mu$m/ml of phytohemaglutinin were placed in Eppendorf tubes. Four subsets were formed (three tubes per subset). The first subset was shielded from the magnetic fields. Subset 2 was exposed to the combination of time-varying electromagnetic fields and static magnetic fields in accordance with this invention. Subset 3 was exposed only to the time-varying electromagnetic fields in accordance with this invention, and Subset 4 was exposed only to the static magnetic field in accordance with his invention. Four subsets were prepared without phytohemaglutinin (controls) and placed under the same experimental conditions.

All tubes were incubated at 37° C. in a $CO_2$ humidifier incubator (Forma Scientific Mod 3325 Dual-Chamber $CO_2$-water jacketed incubator). After an incubation period of 58 hours 1 $\mu$Ci of $^3$H-thymidine (5–6 $\mu$Ci/mM final concentration) was added to all tubes and incubated for an additional 14 hours. All tubes were harvested at 72 hours and washed through glass fiber filter paper with a cell harvester, (Skraton, Tranby, Norway). $^3$H-thymidine incorporation was determined using a liquid scintillator counter (Beckmann Mod LS 6000 SE). The mean number of counts per minute was obtained by triplicate in each sample. Cell viability was always greater than 90% determined on the basis of trypan blue exclusion. FIG. 27 shows the magnetic fields effects on PBMCs obtained from normal subjects.

The combined static and time-varying electromagnetic fields produced an 1% increase in PBMCs proliferation ($P<0.001$ Student "T" test). Time-varying electromagnetic fields alone produced about 67% reduction in cell proliferation ($P<0.001$ Student "T" test). Static magnetic fields have no effect on PBMCs proliferation. Therefore, the in vitro experiments demonstrate an effect of the magnetic fields on isolated PBMCs, which is different for each type of magnetic field or its combination.

In Vivo Effect & Safety Study

Example 2

Effect of EMFs on Body Wounds (Safety and Tolerance Study)

Since electromagnetic fields cross biological tissues, they also produce in vivo effects on circulating PBMCs. The in vivo effects of the time varying electromagnetic fields of this invention, alone or combined with the static magnetic fields, are observed in chronic skin wounds even after only about thirty minutes to one hour of exposing a body part situated far from the lesion site to the EMFs of this invention. In this period of time, it is common to observe the drying of a lesion and a reduction of its diameter.

The magnetic fields generated by the apparatus described herein are below the exposure limits recommended as safe by the World Heath Organization (WHO). However, due to the fact that this is a pioneering procedure, the following study was performed to illustrate the safety of the external application of magnetic fields of this invention on humans. After submitting a letter of voluntary consent to participate in the magnetic field protocol, each patient was subjected to a complete clinical history, physical examination, blood chemistry, cell blood count, and urine analysis before magnetic field exposure was applied. Before, during and after exposure to an electromagnetic field, an electrocardiogram was performed and the blood pressure measured. Three groups of volunteers were formed. The first group was exposed to the electromagnetic field forces (EMFs) for 30 minutes a day, the second group for 30 minutes twice a week, and the third group for 30 minutes once a week. These three cohorts were followed for one year without presenting negative side effects.

In the last 5 years, more than 100 patients have been exposed one to seven hours a day one to seven times a week to external magnetic fields in accordance with the method of this invention. During the course of these treatments, no adverse or negative side effects were observed in any of these patients during or after the period of exposure to EMFs. The application of EMFs by the method and apparatus of this invention showed no effects on their electrocardiograms even in patients who had heart disease. Nor did such treatment have any adverse effects on the patient's motor and sensory nerve function or conduction.

Clinical Trials

The following are clinical trials evidencing the efficacy of the treatment of the invention as applied to the limb of patients with histories of chronic wounds, which were previously unresponsive to other therapeutic treatments.

A Phase I protocol following the Good Clinical Practice Guidelines as defined by the U.S. Food and Drug Administration (Phase I Study) was presented to the Juarez Hospital Institutional Review Board/Ethics Committee and was approved Sep. 24, 1995. Standard operating procedures were followed for monitoring the clinical trial. A total of 42 patients were studied.

The following clinical trials demonstrate the efficacy of the treatment of the invention as applied to the limb of patients with histories of chronic wounds, which were previously unresponsive to other therapeutic treatments and to patients with bone fractures.

Electromagnetic stimulation as defined below was applied in the arm two to three hours a day, several times a week, or a period of two to eight months. All exposed tissues of the arm were considered under the combined effect of the static and/or time variable magnetic fields. The intensity of the induced variable electric fields in each segment of the arm varied with the radius according to Faraday's law.

Twenty five patients were admitted for treatment of chronic leg ulcers. The complete case record for each patient contains a signed voluntary consent form. Their clinical histories include definition of venous and arterial diseases, presence of other underlying diseases, ulcer history and treatments used. Only lesions that remained unhealed at the time of examination were followed up. Each ulcer was described and documented by photographs, its size and approximate area calculated (length×width). When more than one ulcer existed, an approximate total ulcer area was determined. Laboratory tests include blood chemistry, hematological examinations, electrocardiogram and other diagnostic tests. The peripheral circulation was evaluated by doppler-color ultrasonography, arteriography, venography and pletismography. The follow-up records include a periodic photographic registration of chronic leg ulcer history, a weekly clinical commentary and a report of physical examination.

I. Chronic Venous Leg Ulcers

This group included patients whose underlying afflictions were, in addition to the leg ulcers, primary varicose veins, deep vein thrombosis, diabetes, hypertension, rheumatoid arthritis, obesity and cardiovascular disease among others. Pain, edema infection and limited mobility, which accompanied the leg ulcers.

Example 3
Old Female with Primary Varicose Veins

Patient No. 1 is a 75 year old woman afflicted with primary varicose veins and had a 6 $cm^2$ leg ulcer for over 9 months. The ulcer was accompanied by pain, edema and limited mobility. Electromagnetic stimulation in accordance with the invention was then applied to one of her arms for about 2 hours/day 5, days/week over a period of 5 months. No other treatment was administered during this time.

The pain and edema disappeared after the first two weeks of treatment, at which point the patient became fully mobile. The ulcer was covered with granulation tissue and appeared completely healed 5 months after the initiation of the EMFs treatment. As treatment continued, the patient became more alert and optimistic about her life and her memory improved. The patient was kept under observation for a further period of eight months after the ulcer was healed and during all this time, the patient remained asymptomatic.

Example 4
Young Male with Primary Varicose Veins

Patient No. 2 is a 33 year old man afflicted with primary varicose veins, who had a 4 $cm^2$ leg ulcer for over 9 months, which was accompanied by pain and edema. Electromagnetic stimulation in accordance with this invention was applied to his arm for about 2 hours/day 5 days/week for a period of 1 week in the absence of additional treatments.

One week after initiation of the treatment, the pain and edema disappeared and the ulcer appeared completely healed, 6 weeks later, however, when the patient returned to the hospital, he had a new leg ulcer in all appearances produced by trauma, not by reoccurrence.

A second series of EMFs treatment was then applied to one of his arms 2 hours/day for four days. As the first time, the second treatment healed-this ulcer in one week.

Example 5
Middle Aged Female with Primary Varicose Veins

Patient No. 3 is a 66 year old woman that was afflicted with primary varicose veins and had a 6 $cm^2$ leg ulcer for over a year. The ulcer was accompanied by pain, edema, and limited mobility.

The only treatment she received was electromagnetic stimulation, applied to one of her arms 2 hours/day, 3 days/week for a period of 3 months.

After the first 2 weeks of treatment, the pain and edema disappeared and the patient became fully mobile. The treatment enhanced the growth of granulation tissue and reduced the ulcerated area on her leg by about 48%, 3 months after treatment began.

Example 6
Young Female with Deep Vein Thrombosis

Patient No. 4 is a 38 year old woman, afflicted with deep vein thrombosis for over 8 years and had a 6 $cm^2$ leg ulcer for over 7 years. The ulcer was accompanied by pain, edema and limited mobility. During this time, the patient was given medical and surgical treatment, including saphenectomy and skin graft procedures, as well as the application of an ambulatory pressure bandage to the ulcer, but they were ineffective in improving her condition.

Electromagnetic stimulation in accordance with this invention was then applied to one of her arms 2 hours/day, 5 days/week for a period of over 5 months. During this time the patient continued to use her loose ambulatory bandage on the leg ulcer she used before the electromagnetic therapy.

After the first two weeks of treatment the pain and edema disappeared, and after 6 weeks she became fully mobile. After 5 months of treatment the ulcer base was superficial and its size reduced by about 80%.

Example 7
Middle Aged Female with Deep Vein Thrombosis and Superficial Venous Insufficiency Patient No. 5 is a obese 41 year old woman, afflicted with deep vein thrombosis and superficial venous insufficiency, with chronic leg ulcers for over 7 years in both lower limbs. The ulcerated areas were accompanied by pain, edema, itching and limited mobility. During is time, she received local and systemic medical treatment, as well as phlebotomy with Litton technique in both legs which were ineffective in improving her condition.

Electromagnetic stimulation was then applied to one of her arms for 2 hours/day, 3 days/week. After the first two weeks of treatment pain and edema disappeared and in two months the ulcers were completely healed and EMFs exposure was suspended. Four months later, the ulcers remained healed and the patient was asymptomatic.

Example 8
Middle Aged Female with a Deep and Superficial Venous Insufficiency and Arterial Hypertension Patient No. 6 is an obese 59 year old woman, afflicted with deep and superficial venous insufficiency and arterial hypertension, with a chronic leg ulcer for over one and a half years. The ulcer was accompanied by pain, edema, a big area of erythema and limited mobility. During this time, arterial hypertension was kept under control and the ulcer was treated with conventional medical and surgical treatments which were ineffective in improving her condition.

The electromagnetic stimulation was then applied to one of her as for 2 hours/day, 3 days/week for about 2 months while she continued to take the same anti-hypertensive treatment as before. After the first two weeks of electromagnetic therapy pain and edema disappear and in three weeks the ulcer was covered by scab. The area of erythema was reduced in four weeks and the scab began to fall being substituted by scarred tissue.

Example 9
Female with Lymphatic and Superficial Venous Insufficiency

Patient No. 7 is a 42-year-old female afflicted with lymphatic and superficial venous insufficiency caused by a burn on her left leg, which occurred when she was 2 years old. In addition, for a period of over 5 years she had an extensive ulcerated area on her leg totaling 395 $cm^2$, which was accompanied, by pain, edema and limited mobility. During that time, she had received compressive ambulatory bandage, medical and surgical treatments, including skin grafts, which were ineffective in improving her condition.

Electromagnetic stimulation was then applied to one of her arms for 2 hours/day, 5 days/week for a period of over 6 months in accordance with the invention. During the course of this therapy, she continued to use the loose, compressive ambulatory bandage, which she used before electromagnetic therapy. No other additional treatment was administered to her.

After 2 weeks of electromagnetic treatment, the pain and edema disappeared, and after 4 to 8 weeks she became fully mobile. After 4 to 7 weeks of electromagnetic treatment, angiogenesis was evident by the presence of abundant granulation tissue on the ulcerated area. At week 8 she became fully mobile. The lesion was completely healed after 7 months of treatment.

Example 10
Female with Superficial Venous Insufficiency

Patient No. 8 is a 52 year old woman with superficial venous insufficiency who had a 7 cm$^2$ leg ulcer for over 7 years. The ulcer was accompanied by pain, edema, infection and limited mobility. The electromagnetic stimulation was applied to one of her arms for about 2 hours/day, 3 days/week over a period of two months. No other treatment was administered during this time.

The pain and edema disappeared after the first week of treatment at which point the patient become fully mobile. The ulcer size was reduced by more than 95% after 1 month of treatment.

Example 11
Old Female with Superficial Venous Insufficiency

Patient No. 9 is a 62 year old woman afflicted with superficial venous insufficiency and a chronic leg ulcer which opened and closed for over 15 years. A week before admission to the study the ulcer scar became very painful producing a 0.5 cm$^2$ ulcerated area with serum exudate. The electromagnetic stimulation was then applied to one of her arms for about 2 hours/day, 3 days/week for two weeks. The ulcer heated in three days and the patient remained asymptomatic during the following month.

Example 12
Middle Aged Female with Superficial Venous Insufficiency Factitial Ulcer and Mental Depression Patient No. 10 is a 51 year old, mentally depressed woman who had two leg ulcers of approximately 25 cm$^2$ that were artificially maintained open by the patient for over 21 years. The lesions were accompanied by pain, edema and limited mobility. During that time the patient had been given medical treatment but it was ineffective in treating her condition. Electromagnetic stimulation in accordance with this invention was then applied to the patient's arm 2 hours/day, 3 days/week for a period of two months. No other treatment was administered to her during this time.

After 4 weeks of the treatment the pain and edema disappeared, and after 2 months of the treatment the ulcer had been reduced by about 32%.

I.1 Pathologies Associated with Chronic Venous Leg Ulcers and/or Venous Disease That Limit Beneficial Effect This group includes patients whose underlying afflictions are, in addition to the chronic leg ulcers and venous disease, non pitting edema, obesity with very high body mass index (more than 40 kg/M$^2$) and dioderma gangrenosum among others. Pain, edema and infection accompanied the chronic leg ulcers.

Example 13
Superficial and/or Deep Venous Insufficiency, Non-pitting Edema, Obesity & Chronic Venous Leg Ulcers This example describes treatment to a group of four patients. The patients (Patients Nos. 11–14) are one woman and three men 56 to 71 years old afflicted with superficial and/or deep venous insufficiency, brawny edema, obesity and chronic venous leg ulcers for a period of 9 to 17 years. All patients had been with preventively treated with present recommended medical treatments, and surgery intended to alleviate venous hypertension and/or to cover the ulcerated areas with skin grafts. All these treatments were ineffective to improve their condition.

Electromagnetic stimulation in accordance with this invention was then applied to each of patients 11 to 14 on either arm 2 hours/day, 3 days/week. Two weeks after the initiation of EMFs treatment, pain was reduced and the ulcers look dried and deep. These changes improved patient's condition for a while, however the size of the ulcers remained the same and in some cases increased their size during the EMFs treatment period. These patients were eliminated from the protocol.

Example 14
Female with Severe Superficial Venous Insufficiency, Obesity with High Body Mass Index & Chronic Venous Leg Ulcer Patient No. 15 is a 46 year old woman afflicted with superficial venous insufficiency since she was 13 years old, obesity with very high Body Mass Index (more than 40 kg/M2) and a painful large chronic venous leg ulcer in her left leg for a period of over 4 years. During that time, she received preventive measurements and recommended medical treatments in specialized centers without improving her condition.

Electromagnetic stimulation in accordance with this invention was then applied to one of her arms 2 hours/day, 3 days/week, for a period of four months. Two weeks after the initiation of EMFs treatment, pain was reduced, exudate stop and the ulcer borders look inflamed. However the size of the ulcer remained the same during the EMFs treatment period. This patient was eliminated from the protocol.

Example 15
Middle Aged Female with Deep Vein Thrombosis & Pioderma Gangrenosum

Patient No. 16 is a 46 year old woman afflicted with deep vein thrombosis and two atypical ulcers located in the posterior part of her right leg for a period over 4 years. During that time, she received preventive measurements and recommended medical treatments in specialized centers without improving her condition.

Electromagnetic stimulation in accordance with this invention was then applied to one of her arms 2 hours/day, 3 days/week, for a period of four months. Two weeks after the initiation of EMFs treatment, pain was reduced and one of the ulcers became superficial. After that point the ulcers began to grow and the patient was eliminated from the protocol. A skin biopsy revealed changes compatible with Piodernia Gangrenosum the patient was medically treated.

II. Arterial Leg Ulcers

This group consists of patients whose underlying afflictions, in addition to the chronic arterial leg ulcers, were generalized atherosclerosis, diabetes, arterial and/or venous hypertension, rheumatoid arthritis, obesity, cardiovascular disease and vascular necrosis, among others. Rest pain, edema infection and limited mobility accompanied the leg ulcers.

Example 16
Old Woman with Critical Leg Ischemia & Diabetes

Patient No. 17 is a 73 year old woman, afflicted with 3 arterial ulcers and diabetes, who had a 22 cm$_2$ ulcerated area on her left leg for over 4 months accompanied by Dense pain that prevented the patient from sleeping at night. During that time she received medical treatment, but it was ineffective in improving her condition.

Electromagnetic stimulation in accordance with this invention was then applied to one of her arms for 3 hours/ day, 4 days/week for a period of over 7 months. No other treatment was administered during this time.

After 4 weeks of treatment, the skin temperature increased and the superficial veins became more noticeable reflecting increased vasculogenesis. The ulcer bottom display abundant granulation tissue reflecting increased angiogenesis. Pain was greatly reduced allowing the patient to sleep at night. After 7 months of electromagnetic treatment the three ulcers were completely healed. During this time the mental alertness and memory of the patient improved significantly. This patient was followed for an additional year. During this time the ulcers remained healed.

Example 17
Old Woman with Rheumatoid Arthritis & Atherosclerosis

Patient No. 18, is an 80 year old woman afflicted with two arterial ulcers associated with rheumatoid arthritis and atherosclerosis. The ulcerated area was approximately 35 $cm^2$ produced by elastic stockings after knee surgery. These lesions remained open for 19 months and were accompanied by intense pain that kept the patient awake at night. Skin grafts and pharmacological treatments were ineffective in improving her condition. Electromagnetic stimulation in accordance with this invention was applied to one of her arms for three hours/day, 3 days/week, for a period of 4½ months. No other treatment was administered during this time.

Four weeks after the initiation of the electromagnetic treatment pain was reduced, allowing the patient to sleep at night. The skin temperature increased and the superficial veins became more noticeable reflecting increased vasculogenesis. The ulcer bottom display abundant granulation tissue reflecting increased angiogenesis. In two months the patient had no pain and the ulcerated area was completely healed in four and a half months. During this period the patient became more alert, enthusiastic and her memory improved. The patient was followed for an additional eight moths. During tis time the ulcers remained healed.

Example 18
Old Man with Generalized Atherosclerosis

Patient No 19 is a 70 year old man afflicted with a two year old chronic arterial ulcer 65 $cm^2$, caused by generalized atherosclerosis on the anterior part of his leg. The femoral artery lumen was 85% reduced and the anterior tibial artery lumen had 90% stenosis. The ulcer was accompanied by intense pain that kept the patient awake at night. Skin grafts and pharmacological treatments were ineffective in improving his condition.

Electromagnetic stimulation in accordance with this invention was applied to one of his arms for three hours/day, 3 days/week, for a period of 12 months. No other treatment was administered during this time.

After two weeks of treatment the ulcer bottom was red and the tendon was epithelialized, pain was greatly reduced allowing the patient to sleep at night and mobility was improved. After two and a half months, the skin temperature increased and the superficial veins became more noticeable reflecting increased vasculogenesis. The ulcer bottom displayed abundant granulation tissue reflecting increased angiogenesis and the patient was without pain. During this time the patient became more optimistic, alert and his mood improved significantly. The overall reduction of the ulcerated surface area on his leg brought about by 12 months of treatment was about 80%.

Example 19
Female with Generalized Atherosclerosis, Superficial & Deep Venous Insufficiency & Rheumatoid Arthritis Patient No. 20 is a 57-year-old woman afflicted with generalized atherosclerosis, superficial and deep venous insufficiency and rheumatoid arthritis. Additionally, she had two 9 month old ulcers. One ulcerated area 6.5 $cm^2$ on the front part of her leg, and the other a 1 $cm^2$ medial malleolus ulcer. Electromagnetic stimulation was then applied on one of the patient's arms, 3 hours/day, 4 days/week, for about 7 months. No other treatment was administered at this time.

After 3 months of electromagnetic treatment, the medial malleolus ulcer healed and the ulcer in the front part of her leg healed in seven months. During this time her depressive mood improved.

Example 20
Middle Aged Female with Vascular Necrosis

Patient No. 21 is a 45 year old woman afflicted with vascular necrosis of the right leg resulting from receiving a silicon implant. Reconstructive surgery saved her leg from amputation. Two years after, the use of a tight prosthesis lead to arterial occlusion in the posterior-medial area other leg, resulting in a very painful 23 $cm^2$ ulcer that lasted for over 5 months. Pain and edema accompanied the Ulcer, and she had limited mobility. During that time she received medical treatment, but it was ineffective in relieving her condition. Before electromagnetic therapy was given to the patient, she required local anesthesia while her ulcer was cleaned. The electromagnetic stimulation was applied to her arm 1 hour/day, 5 days/week for a period of over 2 months, during which time her ulcer was cleaned daily. No other treatment was administered at this time.

After 4 weeks of treatment the pain and edema disappeared, anesthesia was no longer needed to clean the ulcer, and the patient became fully mobile. Abundant granulation tissue appeared in the ulcer bottom and the ulcer was completely healed after 2 months of the treatment.

Example 21
Middle Aged Male with Uncontrolled Arterial Hypertension & Deep Vein Thrombosis Patient No. 22 is a 54 year old man, afflicted with uncontrolled arterial hypertension and deep vein thrombosis which had chronic leg ulcers totaling 20 $cm^2$ for over 7 years. The ulcerated area was accompanied by pain, edema, and limited mobility. During this time, he received medical treatment, including anti-hypertensive therapy, but it was ineffective in improving his condition.

Electromagnetic stimulation was then applied to one of his arms for 2 hours/day, 3 days/week for about 4 months while he continued to take the same anti hypertensive treatment as before.

After the first 3 weeks of treatment, the pain, edema, and the necrotic tissue of the ulcer disappeared. He became fully mobile after 6 weeks of treatment and the ulcers completely healed in less than 3 months of treatment.

Example 22
Female with Uncontrolled Arterial Hypertension, Superficial Venous Insufficiency, Controlled Type II Diabetes Mellitus & Obesity Patient No. 23 is a 60 year old woman who had 2 leg ulcers totaling 11 $cm^2$ one of which she had for over a year and the other for over 3 months. During that time she received medical treatment including anti-hypertensive therapy, but it was ineffective in improving her condition Electromagnetic stimulation in accordance with the present method was then applied on one of her arms for 3 hours/day, 3 days/week for a period of over 4½ months, during which time she received a continuation of her antihypertensive treatment. During the course of electromagnetic therapy the patient developed a third lesion which was produced by trauma.

After one week of treatment, the pain, edema, and the three-month-old leg ulcer disappeared. The lesion induced by subsequent trauma healed after 6 weeks of electromagnetic treatment. The patient was followed for an additional year and the ulcers remained healed.

Example 23
Old Female with Generalized Atherosclerosis

Patient No. 24 is an 85 year old woman afflicted with generalized atherosclerosis and a chronic leg ulcer 1.2 cm$^2$ for over one year. During that time she received the recommended medical treatment but it was ineffective in relieving her condition.

Electromagnetic stimulation in accordance with the present method was applied to one of her arms 2 hours/day, 5 days/week for a period of over 2 months. After two weeks of treatment the pain and edema disappeared. The changes were followed by a reactivation of the inflammatory reaction around the ulcer with an exuberant increase of granulation tissue that cover the ulcer bottom reflecting enhanced angiogenesis. In three months the ulcerated area was reduced by more than 70%.

Example 24
Young Male with Uncontrolled Type I Diabetes Mellitus & Hypercholesterolemia Patient No. 25 is a 24 year old man afflicted with uncontrolled Type I diabetes mellitus and hypercholesterolemia, afflicted with a three month old plantar ulcer on his left foot. The patient received local surgical and medical treatments that were ineffective in relieving his condition. The electromagnetic stimulation was applied to one of his arms 2 hours/day, 5 days/week for a period of over 2 months. After three weeks of treatment the deep ulcer base was at the level of the dermis. The ulcer healed completely in four weeks. The patient was followed for an additional four months remaining asymptomatic.

III. Pressure Ulcers (Decubitus Ulcers)

This group includes patients whose underlying afflictions were, in addition to the pressure ulcers, paraplegia, deep vein thrombosis and obesity, among others. Pain, edema and infection accompanied the pressure ulcers.

Example 25
Middle Aged Incontinent, Paraplegic Female with Leg Wounds

Patient No. 26 is a 64 year old, paraplegic and incontinent woman who had 2 wounds. The 24 cm$^2$ wound located on her left thigh had been caused by an attempt to surgically repair an electric blanket burn and was 6 months old. The second wound was a 4-month-old, stage 5 Yarkony-Kirk classification decubitus sacrum ulcer. During that time, she received systemic antibiotic treatment and three attempts were made to surgically repair her wounds. Those treatments were ineffective in improving her condition. Electromagnetic stimulation was then applied on one of her arms for 6 hours/day, 7 days/weeks for a period of over 8½ months. The patient received nurse care for 24 hours/day and continued to receive systemic antibiotic treatment. No other additional wound treatment was administered at this time.

After 6 weeks of electromagnetic treatment the thigh wound healed, the decubitus ulcer infection was controlled, and wound retraction and epithelialization continued to heal the wound. After 13 weeks of electromagnetic treatment the abundant granulation and epithelial tissues were removed and the wound was surgically closed after leaving a surgical drainage.

After 3 further weeks of electromagnetic treatment, the surgical wound was healed and an ulcerated area was formed at the surgical drainage. An autologous skin graft placed on the ulcer site was eventually lost. The decubitus ulcer healed completely after three additional months of electromagnetic therapy.

Example 26
Old Female with Pressure Ulcer & Deep Vein Thrombosis

Patient No. 27 is an obese 90 year old woman who had an 18 month old, 60 cm$^2$ painful, edematous, bleeding, friable, purple, deep pressure ulcer on her left ischial tuberosity caused by her sitting in the same position for 8 to 12 hours/day while being afflicted with deep vein thrombosis. Pain and edema accompanied the ulcer. During that time, the patient received medical treatment including local wound cleaning, but the treatment was ineffective in improving her condition.

Electromagnetic stimulation was then applied to one of her arms for 2 hours/day, 7 days/week for a period of over 5 months. She continued to receive local wound cleaning, but no additional treatment was given to her at this time.

After 2 weeks of electromagnetic treatment the pain and edema disappeared, except for a 1×10 mm open skin area which did not heal because of the constant pressure from sitting. During the course of treatment, her skin resistance increased. The color of the skin was pink in the morning and bright red after 8 to 12 hours of sitting. After 4 months of treatment, the ulcer was completely healed and the skin returned to normal.

IV. Chronic Wounds

This group included patients whose underlying afflictions were, in addition to the chronic wounds, peripheral arterial disease, intense stress and peritonitis, among others. Pain, edema and infection accompanied the chronic wounds.

Example 27
Old Male with Infected Surgical Wound

Patient No. 28 is a 78 year old man who had a 126 cm$^2$ infected surgical wound after a long and complicated abdominal surgery.

Electromagnetic stimulation was applied to one of his arms 1 hours/day for 3 weeks. After 2 weeks of treatment the infection disappeared, and the wound was surgically closed because of granulation tissue and wound healing were under optimal conditions for this procedure.

Example 28
Old Man with Unhealed Surgical Wounds

Patient No. 29 is a 73 year old man with lower limb arterial disease associated with smoking, diabetes and generalized atherosclerosis. Chronic lower-limb ischemia had been present for years. Critical leg ischemia was evident in the last year and the patient was subjected to surgical re-vascularization. However, 3½ months after the operation, the surgical wounds located in his left thigh and leg were not healed and the knee surgical wound remained an open 30 cm$^2$ wound.

Electromagnetic stimulation in accordance with this invention was then applied to one of his arms 2 hours/day 3 days/week for a period of five months. No additional treatment was administered to him.

After 4 weeks of electromagnetic treatment the thigh and leg wounds healed and wound retraction and epitheialization continued to heal the knee wound, reducing the wound area to about 97% in 5 months. The wound was completely healed in one additional month.

Example 29
Middle Aged Female with an Unhealed Ulcer

Patient No. 30 is a 65 year old woman with lower limb arterial disease associated with smoking. As a consequence of a trauma, a small bruise developed into a 2.6 cm² infected, very painful ulcer, in two weeks causing reduced mobility. This wound was resistant to antibiotic treatment.

Electromagnetic stimulation in accordance with this invention was then applied to one of her arms 2 hours/day, 5 days/week in addition to a new antibiotic treatment. After two weeks the infection was controlled, edema and pain were drastically reduced and mobility became almost normal. The previously unhealed wound displayed abundant granulation tissue on the ulcer bottom. A week later the patient was asymptomatic and ulcer healed in less than one month since the beginning of EMFs treatment.

Example 30
Middle Age Male with an Infected Shoulder Wound

Patient No. 31 is a 57 year old man under intense stress who by scratching an old scar developed a 3 cm³ very painful abscess in his left shoulder in two weeks. The lesion was controlled with antibiotics but two weeks later pain, edema, immobility and a 3 cm² open wound were still present.

Electromagnetic stimulation in accordance with his invention was then applied to one of his arms 2 hours/day, 5 days/week. Three weeks later, pain, edema and immobility disappeared and the wound was reduced by more than 70%. The ulcer healed completely two weeks later.

V. Dilated Ischemic Cardiomyopathy

This group includes patients with viable but underperfused myocardium, who were not candidates for coronary revascularization.

Atherosclerosis is a generalized disease responsible for occlusive arterial disease such as lower-limb arterial disease (chronic arterial leg ulcers), myocardial infarction and stroke. The etiological factors (arterial hypertension, high serum cholesterol, smoking, stress, diabetes mellitus) are similar, as are preventive measurements (eliminate or control the etiological factors), and some treatments (angioplasty or by-pass when indicated). The enhancement of the body's natural process of collateral blood vessel growth is a novel approach. Therapeutic angiogenesis has been attempted using angiogenic growth factors. Acid and basic fibroblast growth factors have been successfully tested in animal models but positive clinical results have not been reported in clinical trials. Vascular endothelial growth factor (VEGF) recombinant protein has been successfully tested in patients with heart infarction that were not ideal candidates for coronary revascularization and intramuscular injection of naked plasmid DNA encoding the 165 isoform of VEGF has been successfully tested in patients with critical limb ischemia.

Example 31
Young Male with Sequela of Anteroseptal Acute Myocardial Infarction Patient No. 32 is a 40 year old man with sequela of anteroseptal acute myocardial infarction. The patient was evaluated by clinical examination, blood tests, chest X-Ray, electrocardiogram, stress test, echocardiogram, coronary angiography, and cardiac ventriculography. The observed lesions include anteroseptal myocardial infarction with extensive anterior and lateral sub-epicardic ischemia and left bundle anterior hemi-branch block. 90% stenosis in middle third of left anterior descending coronary artery with a severe stenosis of first diagonal artery at its origin, slow TIMI 2 flow, anterior, apical, inferior and septal akinesis. Ejection fraction 20%. Patient was classified as Functional Class III of the New York Heart Association (NYHA) being not candidate for coronary revascularization. Patient remained on isorbide 10 mg 3/day, aspirin 150 mg/day and rest during four additional months without showing any improvement. Electromagnetic force (EMFs) was then applied to one of his arms 2 hours/day, 3 days/week for a period of one month while continuing with the same medical treatment as before.

After one month of EMFs treatment, patient improvement was very fast even in the presence of bad evolution of the left descending coronary artery lesion that changed from 90% stenosis to occlusion. Clinical evaluation and stress test classified the patient in Functional Class I of the New York Heart Association (NYHA), instead of the Class III he had before. Anterior, apical, inferior and septal akinesis diagnosed by ventriculograin and echocardiogram improved to hypokinesis. Collateral circulation and contractility of hybernating myocardium improved.

These changes may not be explained by the medical treatment he received during four months after AMI and previously to be exposed to EMFs. During all this period the patient remained in Functional Class III (NYHA). The most plausible explanation for the patient's better clinical condition in only one month after EMFs exposure, Functional Class I (NYHA), is enhanced angiogenesis and vasculogenesis in viable but underperfused myocardium induced by the EMFs activated peripheral blood mononuclear cells.

Example 32
Obese Woman with Arterial Hypertension & Sequela of Three Month Old Acute Myocardial Infarction Patient 33 is a 54 year old obese woman afflicted with arterial hypertension and sequela of a three month old Acute Myocardial Infarction (AMI). Patient evaluation included clinical examination, blood tests, chest X-Ray, electrocardiogram, stress test, echocardiogram, coronary angiography, and cardiac ventriculography. Lesions included Arterial Hypertension, elevated blood values of Glucose, Uric Acid, Triglycerides and Cholesterol. Anteroseptal and lateral subendocardic necrosis. Extensive anterior sub-epicardic ischemia. Right atrium enlargement. Coronary angiogram. reported occlusion of left descending coronary artery at its origin and 80% stenosis of circumflex. Patient was treated with Metoprolol 50 mg./12 Hs., Isorbide 10 mg./12 Hs., Pravacol 20 mg./24 Hs. Norvas 2.5 mg./24 Hs. and ASA 100 mg./24 Hs. Tree months later arterial hypertension and blood tests were within normal limits but the cardiovascular symptomatology deteriorated, from Functional Class II New York Heart Association (NYHA) to Functional Class III (NYHA). An stress test was attempted but had to be suspended at the beginning of the test by fatigue, hypertension and pain. Functional Class III (NYHA).

Electromagnetic stimulation was then applied to one of her arms 2 hours/day, 4 days/week for a period of five months while continuing with her previous treatment.

After one month of EMFs treatment, patient evaluation changed from Functional Class III (NYHA) to Functional Class I (NYHA) and collateral circulation and contractility of hibernating myocardium improved. These changes occur in the presence of more severe lesions than the ones observed in her previous coronary angiogram including additional occlusion of the right coronary artery at its middle third, 90% stenosis of the first diagonal artery and left ventricle diastolic final pressure of 15 mm Hg.

These changes in only one month after EMFs may not be explained by the medical treatment she received during nine months after AMI and previously to be exposed to EMFs. During all this period the patient evolved from Functional Class II (NYHA) to functional class III (NYHA). The most plausible explanation for the patient's better clinical condition, Functional Class I (NYHA), are enhanced angiogenesis and vasculogenesis in viable but underperfused myocardium induced by the EMFs activated peripheral blood mononuclear cells.

VI. Ankle Fractures

This group included patients with no other underlying affliction. This orthopaedic problem was selected to evaluate the benefits of the EMFs of this invention in reducing pain and edema in an acute problem as well as to observe if it could accelerate the healing process of a different type of internal wound, i.e. a bone fracture.

Example 33

Eight Patients with Ankle Fractures Type Weber A or B

This example presents information on a group of eight patients (patients 34 to 41). The patients are two women and six men 19 to 65 years old, afflicted with uni or bi-malleolar ankle fractures type Weber A or B. All fractures were accompanied with intense pain, and edema. All fractures were treated with internal fixation. Compression of fracture surfaces was obtained with lag screws with or without semitubular compression plates. Surgical repair of the deltoid ligament was done when indicated. Sterile dressings were applied to the wounds and then a plaster splint to hold the foot in neutral position.

Electromagnetic stimulation was then applied to each patient on either arm 2 hours/day, 2–3 days/week for 10 sessions beginning the next day after surgery. Leg was maintained elevated and pain was controlled with Dipirone 500 mg 3/day.

In all patients, pain was reduced from 10 to 34 days. Edema from 10 to 5–6 days and bone union was observed in four weeks instead of six, at that point patients were allowed full-weight bearing.

VII. Spinal Muscular Atropies

This patient was selected as an example of nerve regeneration in a disease with no present treatment. In partial denervation, the axon and the nerve terminal innervating a muscle fiber degenerates. Healthy denervated tissue responds by releasing cytokines that induce the terminal Schwann cells on the denervated muscle fiber to grow processes that reach the nerve terminal of a neighboring innervated muscle fiber. Then the Schwann cell process induce a nerve sprout in the normal nerve terminal that grows along the Schwann cell process towards the denervated endplate until reinnervation of the denervated endplate is completed. At early stages of certain types of spinal muscular atrophies when a motor neuron of the spinal cord dies, cytokine signaling language stimulated by EMF's activated PBMCs could trigger these events in neighboring healthy axons not affected by the disease producing reinervation of the denervated muscle fibers.

Example 34

Young Boy with Spinal Muscular Atrophy

Patient 42 is a 4 year old boy with Spinal Muscular Atrophy. Being the second boy of a normal twin pregnancy and delivery, their parents had the benefit to compare one twin to the other. Their recollection suggests that early development was delayed. He started walking at 15 months but his gait appeared abnormal and since age 2 he has been unable to run or hop, has difficulty walking up one or two steps, tends to fall frequently and needs help getting back on his feet. At physical examination weakness of all muscle groups was noticeable but more so in the shoulder and pelvic girdles. These findings together with the subtle fasciculations of the tongue, electromyography, magnetic resonance imaging and left quadriceps biopsy support the diagnosis of Spinal Muscular Atrophy. During the last year, diets, rehabilitation therapy and the use of stabilizing artroses have been ineffective in improving his condition.

After signing a voluntary consent form, electromagnetic stimulation was then applied to one of his arms, 2 hours/day, 2 days/week for one month, however this was difficult to achieve because of his age. Therefore, a new design with Hemholtz coils was used to expose part of the body while the child was sleeping. This modality of electromagnetic stimulation was applied 2 hours/day, 5 days/week for a period of two years.

Periodic examinations by the inventor, the pediatrician, the neurologist, the rehabilitation specialist, notes of the mother and teacher, and videotapes, were used to follow his evolution. After the first month his equilibrium was better, more confident to play with his brother, sister and peers at school. He started gaining weight, and at 4 months he was able to walk without falling and began to run and hop. At six months, an increase in muscular strength and mass of the shoulder and pelvic girdles was noticeable. One year after the initiation of treatment the child was able to rise from the floor without help. Two years after, his movements and development were almost normal.

Conclusions

The above examples show that the application of external, non-invasive electromagnetic fields (EMFs) in accordance with the method of this invention, either alone or combined with other medical and surgical treatments healed body lesions in patients who were previously unresponsive to conventional medical and surgical treatments alone, or improve the effects of these treatments.

Thus, from the foregoing detailed description of the invention, and the illustrative examples provided herein, it may be appreciated that the treatment offers a remarkably effective clinical means for improving a patient's health and well being without producing adverse or negative side effects. This has been exemplified on patients with various diseases and conditions, such as a history of partial denervation, internal or external lesions such as wounds, areas with inadequate blood perfusion such as viable but underperfused myocardium and the like, burns and ulcers alone or where the patient is suffering from other disorders as well.

What is claimed as being novel & unobvious in Letters Patent of the United States:

1. A method of treating a body lesion(s) associated with inadequate blood perfusion, tissue loss, partial denervation, pain, edema, bone fractures or bone unions, chronic wounds, chronic ulcers, and/or infection, comprising applying to a subject afflicted with the lesion, externally and non-invasively, and at a site removed from the lesion(s), angiogenic, vasculogenic, nerve regeneration, osteogenic, wound repairing, analgesic, anti-edema and/or anti-inflammation effective electromagnetic fields (EMFs) comprising frequencies of about 2 Hertz to less than about 300 Hz and static magnetic field components from about 2 $\mu$T to about 0.8 mT.

2. The method of claim 1, further comprising applying a homogeneous static magnetic field of about 40 to about 80 mT (about 400 to about 800 Gauss).

3. The method of claim 1, wherein the EMFs are applied to the subject's body or a portion thereof.

4. The method of claim 1, wherein the body portion comprises a limb.

5. The method of claim 1, which is conducted for a period of time effective to expose the subject's entire blood volume at least once to the EMFs.

6. The method of claim 1, wherein the EMFs are reapplied periodically.

7. The method of claim 6, wherein the body lesion is selected from a group consisting of burns, traumatic lesions, inadequate blood perfusion, partial denervation, necrotic tissue, wounds and ulcers.

8. A method of treating a disease or condition associated with a body lesion, comprising conducting the method of claim 1, wherein the EMFs are applied for a period of time effective to induce healing of the body lesion.

9. The method of claim 8, wherein the lesion is selected from a group consisting of varicose veins, diseases and conditions accompanied by pain, edema and inflammation, limited mobility, deep vein thrombosis, arterial hypertension, lesions produced by trauma and surgery, lymphatic and venous insufficiencies, ulcers, vasculitis, partial denervation, bone fractures, bone unions, chronic wounds, chronic ulcers, varicose veins, rheumatoid arthritis, vascular necrosis, chronic wounds, and burns.

10. The method of claim 9, wherein the ulcers are selected from a group consisting of venous ulcers, arterial ulcers, decubitus ulcers, deep pressure ulcers, medial malleolus ulcers, factitial ulcers, ulcers produced by trauma and surgery and lower limb ulcers.

11. The method of claim 10, wherein the ulcers are located on the subject's leg or foot.

12. The method of claim 8, wherein the wounds are selected from a group consisting of surgical and non-surgical wounds.

13. The method of claim 12, wherein the non-surgical wounds are selected from a group consisting of tight wounds and Stage 5 Yarkony-Kirk classification decubitus ulcers.

14. The method of claim 12, wherein the wounds are caused by surgery or by surgical drainage.

15. The method of claim 8, wherein the deep vein thrombosis is associated with long periods of inactivity.

16. The method of claim 9, wherein the disease or condition is associated with myocardial infarction, cerebral infarction and/or partial denervation.

17. The method of claim 9, wherein the vascular necrosis is associated with a silicone implant(s).

18. The method of claim 1, further comprising using a treatment for a body lesion(s) associated with pain, partial denervation, bone fractures, bone unions, chronic wounds, chronic ulcers, edema and/or inflammation
wherein the EMFs are applied for a period of time effective to promote the subject's responsiveness to the treatment and alleviate the body lesion(s).

19. The method of claim 18, wherein the subject has become resistant to an agent for treating the disorder or condition prior to applying the magnetic field.

20. The method of claim 18, wherein the treatment is selected from the group consisting of pharmaceutical or surgical treatments.

21. The method of claim 20, wherein the pharmaceutical and surgical treatments are selected from a group consisting of a saphenectomy, skin grafts, surgery, wound closure, stitching, bandaging, anti-hypertensive therapy, pharmaceutical composition administration, nursing care and body lesion clean up.

22. The method of claim 20, wherein the pharmaceutical treatment comprises the administration of a composition comprising an agent selected from a group consisting of the administration of pain killers, anti-inflammatory agents, antibiotics, flavinoids, tissue plasminogen activator, aspirin, prostacyclin analogs, prostanoids, venotonic drugs, fibrinolytic and thrombolytic agents, B-blockers, angiotensin converting enzyme inhibitors, and edible diets.

23. The method of claim 8, wherein the body lesions or diseases are accompanied by inadequate blood perfusion.

24. The method of claim 1, wherein the subject is selected from a group consisting of humans and non-human animals.

25. The method of claim 8, wherein the disease or condition is associated with underperfused myocardium.

26. The method of claim 8, wherein the disease or condition is associated with diabetes.

27. The method of claim 26, wherein the disease or condition is associated with a diabetic foot.

28. The method of claim 8, wherein the disease or condition is associated with an ankle fracture.

29. The method of claim 28, wherein the ankle fracture is accompanied by pain, edema, and/or bone fracture.

30. The method of claim 8, wherein the disease or condition is associated with denervation or infection.

31. The method of claim 8, wherein the disease or condition is associated with reduced brain circulation and/or reduced mental alertness.

32. The method of claim 8, wherein the disease or condition is associated with devascularization.

33. An apparatus for generating time-varying electromagnetic field having frequencies of about 2 Hz to less than about 300 Hz and static magnetic field components from about 2 $\mu$T to about 0.8 mT, comprising
a housing having interior and exterior surfaces, a face panel having an opening, and an elongated annular passage defined by the interior surface of the housing which extends longitudinally from the opening; and
a magnetic coil disposed within the housing and around the elongated annular passage for generating a time-varying electromagnetic field of frequencies of about 2 Hz to less than about 300 Hz and static magnetic field components from about 2 $\mu$T to about 0.8 mT in response to an electric current.

34. The apparatus of claim 33, wherein the housing is rectangularly shaped.

35. The apparatus of claim 33, wherein the housing is shaped as a square and the opening is circular.

36. The apparatus of claim 35, wherein the housing is made from a non-magnetic material.

37. The apparatus of claim 36, wherein the non-magnetic material is selected from the group consisting of wood and plastic.

38. The apparatus of claim 36, further comprising a timer and a control mechanism, both connected to an electronic panel, for varying and controlling the intensity and duration of the electromagnetic field generated by the magnetic coil.

39. An apparatus for simultaneously generating a time-varying electromagnetic field having frequencies of about 2 Hz to less than about 300 Hz and static magnetic field components from about 2 $\mu$T to about 0.8 mT, comprising
a housing with an elongated annular passage formed therethrough; and
a magnetic coil disposed within the housing and around the elongated annular passage for generating a time-varying electromagnetic field of frequencies of about 2 Hz to less than about 300 Hz and static magnetic field components from about 2 $\mu$T to about 0.8 mT in response to an electric current.

40. The apparatus of claim 39, wherein the housing is cylindrically shaped.

41. The apparatus of claim 40, wherein the housing is sized to comfortably accommodate the limb of a patient.

42. The apparatus of claim 41, wherein the housing is made from a light non-magnetic material.

43. The apparatus of claim 42, wherein the non-magnetic material is selected from the group consisting of wood and plastic.

44. The apparatus of claim 42, further comprising an adapter box including a pair of contacts connectable to a power source, a transformer, a rectifier bridge, and two cables extending from the adapter box to provide current to the magnetic roll of the apparatus.

45. An apparatus for generating a time-varying electromagnetic field having frequencies of about 2 Hz to less than about 300 Hz and static magnetic field components from about 2 $\mu$T to about 0.8 mT, and a static magnetic field of about 40 mT to about 80 mT, comprising a housing having interior and exterior surfaces, a face panel having an opening, and an elongated annular passage defined by the interior surface of the housing which extends longitudinally from the opening;

a pair of opposed parallel magnetic members disposed within the housing and around the elongated annular passage for generating a static magnetic field; and a magnetic coil mounted interiorly of the magnetic members for generating a time-varying electromagnetic field of frequencies of about 2 $\mu$z to less than about 300 Hz and static magnetic field components from about 2 $\mu$T to about 0.8 mT, and a static magnetic field of about 40 mT to about 80 mT in response to an electric current.

46. The apparatus of claim 45, wherein the housing is rectangularly shaped.

47. The apparatus of claim 45, wherein the housing is shaped as a square and the opening is circular.

48. The apparatus of claim 46, wherein the housing is made from a non-magnetic material.

49. The apparatus of claim 48, wherein the non-magnetic material is selected from the group consisting of wood and plastic.

50. The apparatus of claim 48, further comprising a timer and a control mechanism, both connected to an electronic panel, for varying and controlling the intensity and duration of the electromagnetic field generated by the magnetic coil.

51. An apparatus for generating a time-varying electromagnetic field having frequencies of about 2 Hz to less than about 300 Hz and static magnetic field components from about 2 $\mu$T to about 0.8 MT, and a static magnetic field of about 40 mT to about 80 mT, comprising a circular shaped housing having an interior diameter sized for permitting a human to lie therein;

a pair of opposed parallel magnetic members for generating a static magnetic field mounted within the circular shaped housing; and a magnetic coil disposed within the circular shaped housing for generating a time-varying electromagnetic field of frequencies of about 2 $\mu$T to less than about 300 Hz and static magnetic field components from about 2 $\mu$T to about 0.8 mT, and a static magnetic field of about 40 mT to about 80 mT in response to an electric current.

52. The apparatus of claim 51, wherein the housing is made from a non magnetic material.

53. The apparatus of claim 52, wherein the non-magnetic material is selected from the group consisting of wood and plastic.

54. The apparatus of claim 52, further comprising a timer and a control mechanism, both connected to an electronic panel, for varying and controlling the intensity and duration of the electromagnetic field generated by the magnetic coil.

55. An apparatus for generating a time-varying electromagnetic field having frequencies of about 2 Hz to less than about 300 Hz and static magnetic field components from about 2 $\mu$T to about 0.8 mT, comprising a circular shaped housing having an interior diameter sized for permitting a human to lie therein; and a magnetic coil disposed within the circular shaped housing for generating a time-varying electromagnetic field of frequencies of about 2 Hz to less than about 300 Hz and static magnetic field components from about 2 $\mu$T to about 0.8 mT in response to an electric current.

56. The apparatus of claim 55, wherein the housing is made from a non-magnetic material.

57. The apparatus of claim 56, wherein the non-magnetic material is selected from the group consisting of wood and plastic.

58. The apparatus of claim 56, further comprising a timer and a control mechanism, both connected to an electronic panel, for varying and controlling the intensity and duration of the electromagnetic field generated by the magnetic coil.

59. An apparatus for generating a time-varying electromagnetic field having frequencies of about 2 Hz to less than about 300 Hz and static magnetic field components from about 2 $\mu$T to about 0.8 mT, comprising a housing having a pair of opposed sidewalls, the sidewalls spaced far enough apart for permitting a human to lie therebetween; and a pair of opposed parallel Hemholtz magnetic coils, each coil mounted in one of the opposed sidewalls for generating a time-varying electromagnetic field of frequencies of about 2 Hz to less than about 300 Hz and static magnetic field components from about 2 $\mu$T to about 0.8 mT therebetween in response to an electric current.

60. The apparatus of claim 59, wherein the housing is made from a non-magnetic material.

61. The apparatus of claim 60, wherein the non magnetic material is selected from the group consisting of wood and plastic.

62. The apparatus of claim 60, further comprising a timer and a control mechanism, both connected to an electronic panel, for varying and controlling the intensity and duration of the electromagnetic field generated by the magnetic coil.

63. An apparatus for generating a time-varying electromagnetic field having frequencies of about 2 Hz to less than about 300 Hz and static magnetic field components from about 2 $\mu$T to about 0.8 mT, comprising a saddle-shaped housing; and a magnetic coil with its coils arranged in a saddle-shaped disposition such that the coil fits within the saddle-shaped housing for generating a time-varying electromagnetic field of frequencies of about 2 Hz to less than about 300 Hz and static magnetic field components from about 2 $\mu$T to about 0.8 WT in response to an electric current.

64. The apparatus of claim 63, wherein the housing is made from a nonmagnetic material.

65. The apparatus of claim 64, wherein the non-magnetic material is selected from the group consisting of wood and plastic.

66. The apparatus of claim 64, further comprising a timer and a control mechanism, both connected to an electronic panel, for varying and controlling the intensity and duration of the electromagnetic field generated by the magnetic coil.

* * * * *

UNITED STATES PATENT AND TRADEMARK OFFICE
CERTIFICATE OF CORRECTION

PATENT NO.     : 6,733,435 B2
DATED          : May 11, 2004
INVENTOR(S)    : Luis Canedo It is certified that error appears in the above-identified patent and that said Letters Patent is hereby corrected as shown below:

<u>Title page</u>,
Item [76], should read:
-- [76] Inventor: Luis Cañedo, Tzompantle No. 7, Col Palmira.
             Cuernavaca Morelos C.P. 64290(MX) --

Signed and Sealed this

Thirty-first Day of August, 2004

JON W. DUDAS
*Director of the United States Patent and Trademark Office*